United States Patent
Kirsch et al.

[11] Patent Number: 6,114,349
[45] Date of Patent: Sep. 5, 2000

[54] SUBSTITUTED QUINOLINE DERIVATIVES WITH ANTIVIRAL ACTION

[75] Inventors: Reinhard Kirsch, Braunschweig; Jörg-Peter Kleim, Niedernhausen; Günther Riess, Hattersheim; Bernd Rosenstock, Neu-Isenburg; Manfred Rösner, Eppstein; Irvin Winkler, Liederbach, all of Germany

[73] Assignee: Hoechst Aktiengesellschaft, Frankfurt am Main, Germany

[21] Appl. No.: 09/155,647

[22] PCT Filed: Mar. 25, 1997

[86] PCT No.: PCT/EP97/01496

§ 371 Date: Mar. 3, 1999

§ 102(e) Date: Mar. 3, 1999

[87] PCT Pub. No.: WO97/37977

PCT Pub. Date: Oct. 16, 1997

[30] Foreign Application Priority Data

Apr. 4, 1996 [DE] Germany ............... 196 13 591

[51] Int. Cl.[7] .............. A61K 31/47; C07D 215/16; C07D 215/38; C07D 215/12; C07D 215/20

[52] U.S. Cl. ............... 514/311; 546/156; 546/152; 546/159; 546/168; 546/170; 546/172; 546/157; 546/178; 546/173; 546/180; 514/312; 514/313; 514/314

[58] Field of Search .................. 546/155–160, 546/168, 170, 152, 172, 176, 178, 173, 180; 514/312, 311, 314, 313

[56] References Cited

FOREIGN PATENT DOCUMENTS

| 0509398A1 | 10/1992 | European Pat. Off. . |
|---|---|---|
| 0579968A1 | 1/1994 | European Pat. Off. . |
| WO 93/11115 | 6/1993 | WIPO . |

OTHER PUBLICATIONS

M. S. Hirsch, "Azidothymidine," J. Infect. Dis., vol. 157, No. 3, pp. 427–431, Mar. 1988.

M. Senthil et al., "Synthesis of Thieno[2,3–b]quinolines–A Convenient Approach," Ind. J. Chem., vol. 28B, pp. 1017–1020, Dec. 1989.

H. Hayashi et al., "5–HT$_3$ Receptor Antagonists. 1. New Quinoline Derivatives," J. Med. Chem., vol. 35, pp. 4893–4902, 1992.

P. Julian et al., "Studies in the Indole Series. XIV. Oxindole–3–Acetic Acid," J. Am. Chem. Soc., vol. 75, pp. 5305–5309, Nov. 5, 1953.

A. Ide et al., "Photoreaction of 4–Substituted Quinoline N–Oxide and 2(1H)–Quinolinone in Propionic Acid," Bull. Chem. Soc. Japan, vol. 50, No. 8, pp. 1959–1963, Aug., 1977.

L. Mastafanova et al., Chemical Abstracts, vol. 89, No. 5, Abstract No. 43065e, p. 598, Jul. 1978.

H. Hayashi et al., Chemical Abstracts, vol. 118, No. 5, Abstract No. 38750n, p. 668, Feb. 1, 1993.

K. Suzuki et al., Chemical Abstracts, vol. 121, No. 15, Abstract No. 179581g, p. 1081, Oct. 10, 1994.

R. Fujita et al., Chemical Abstracts, vol. 124, No. 13, Abstract No. 175786s, p. 1264, Mar. 25, 1996.

*Primary Examiner*—Zinna Northington Davis
*Assistant Examiner*—Binta Robinson
*Attorney, Agent, or Firm*—Finnegan, Henderson, Farabow, Garrett & Dunner, L.L.P.

[57] ABSTRACT

Substituted quinoline derivatives, processes for their preparation, and their use.

Compounds of the formula I

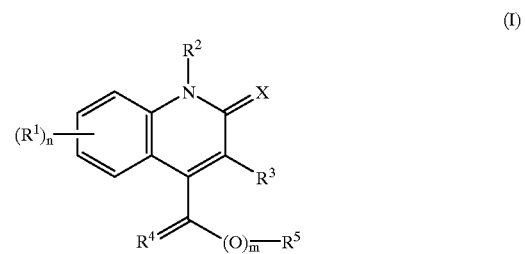

(I)

and their tautomeric forms, of the formula Ia

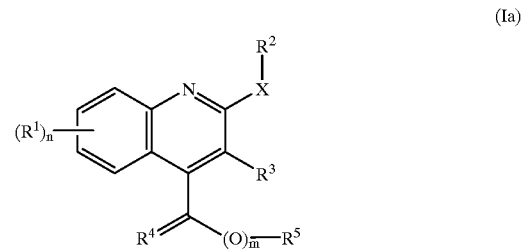

(Ia)

in which m, n and the substituents X and $R^1$ to $R^5$ have the meanings mentioned, have an action against viruses.

19 Claims, No Drawings

SUBSTITUTED QUINOLINE DERIVATIVES WITH ANTIVIRAL ACTION

The present invention relates to quinoline-4-carboxylic acid derivatives and related compounds, processes for their preparation, and their use.

Viral infections in man and animals, in particular in man, are widespread. In spite of intensive efforts, up to now, however, there has still been no success in finding chemotherapeutics which causally or symptomatically interfere with the course of the disease, which is caused virally or retrovirally, with a recognizably substantial success. Treatment of viral and, in particular, retroviral disorders by means of chemotherapeutics is therefore only very imperfect. On account of the highly increasing number of people globally who are infected with the HIV virus, this type of retroviral virus infection in particular is a growing problem worldwide.

The retrovirus called human immunodeficiency virus (HIV) is assumed, inter alia, to be the cause of the complex disease which is called AIDS (Acquired Immune Deficiency Syndrome). AIDS causes a progressive destruction of the immune system of the sick person, associated with a destruction of the peripheral and of the central nervous system. An important step in the replication cycle of retroviruses is the reverse transcription of the RNA genome of the virus by the endogenous virus enzyme reverse transcriptase, which produces DNA copies of the HIV sequence. It is known that some compounds, such as, for example, azidothymidine (AZT), can function as inhibitors of reverse transcriptase. They are therefore used for the treatment of AIDS. AZT and similar compounds of the nucleoside type such as DDC or DDI, however, are characterized by a very narrow therapeutic breadth or by very severe toxicity which occurs even in the therapeutic range (see, for example, Hirsch, M. S. J. Infect. Dis. 157 (1988), 427–431). In addition, the problem of formation of resistance against chemotherapeutics is still largely unsolved.

Iminoquinoline derivatives having antiviral activity against the HIV virus are described in the patent application EP 93109965.9. Quinoxalinone derivatives with related structures having antiviral activity are described in the patent application EP 509.398.

The 4-cyano-substituted quinoline-2(1H)-thiones of the formulae a and b are known from the literature (see Senthil et al., Ind. J.Chem., Sect. B. 1989, 28B (12), 1017–209).

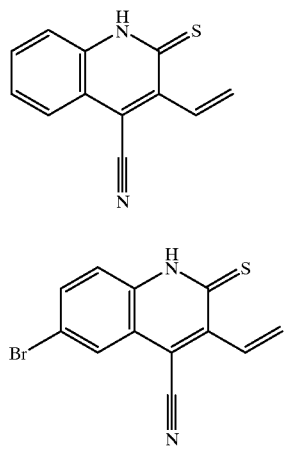

Compounds of the general structure c where R' is hydrogen, alkyl, aryl or benzyl, R" is hydrogen, alkyl and R'" is 3-tropanol (N-8-methyl-8-azabicyclo[3.2.1]octan-3-ol or endo N-8-methyl-8-azabicyclo[3.2.1]oct-3-ylamine have been proposed as potential 5-HT$_3$ receptor antagonists (J. Med. Chem. 1992, 35, 4893–4902)

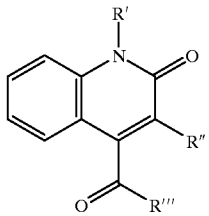

The preparation of the 2-oxo-1,2-dihydroquinolinecarboxylic acid d starting from isatin and malonic acid or 2-oxindole is likewise known from the literature (J. Am. Chem. Soc. 75 (1953), 5305). The preparation of 2-oxo-1,2-dihydro-3-ethylquinolinecarboxylic acid (e) from 2-oxindole and 2-oxobutyric acid is carried out in a similar manner (Bull. Chem. Soc. Jpn., Vol. 50 (8) (1977), 1959–63).

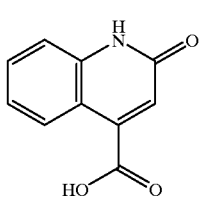

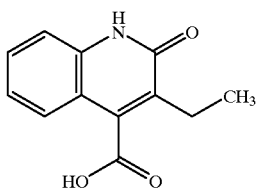

In the patent application WO 93/11115 2-(1H)-quinolinone derivatives of the formula f having an aryl substituent in the 3-position and R equal to an alkoxycarbonyl substituent are claimed as selective noncompetitive NMDA and/or AMPA receptor antagonists for the treatment of diseases such as, for example, neurodegenerative disorders or schizophrenia. An antiviral activity of these derivatives, however, is not mentioned anywhere.

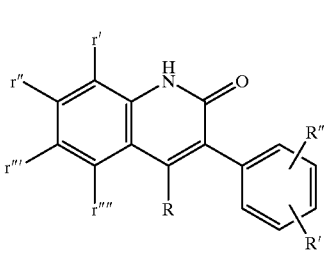

It has now surprisingly been found that certain quinoline derivatives have a high antiviral activity, in particular against the human immunodeficiency virus (HIV).

The invention accordingly relates to compounds of the formula I

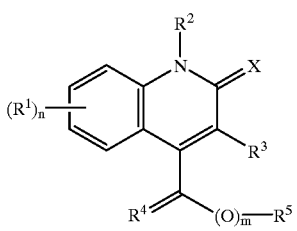

(I)

and their tautomeric forms, of the formula Ia

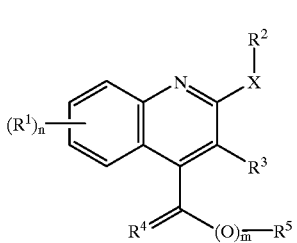

(Ia)

in which:
I)
n is zero, one, two, three, or four,
the individual substituents $R^1$ independently of one another are fluorine, chlorine, bromine, iodine, trifluoromethyl, trifluoromethoxy, hydroxyl, alkyl, cycloalkyl, alkoxy, alkoxy(alkoxy), alkylthio, alkylsulfinyl, alkylsulfonyl, nitro, amino, azido, alkylamino, dialkylamino, piperidino, morpholino, 1-pyrrolidinyl, acyl, acyloxy, acylamino, cyano, carbamoyl, carboxyl, alkyloxycarbonyl, hydroxysulfonyl, sulfamoyl or a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, heteroaroyl, heteroaryl or heteroarylmethyl radical, which is optionally substituted by up to five radicals R which are independent of one another, where $R^6$ can be
fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, alkyloxycarbonyl, phenyl, phenoxy or heteroaryl, X is oxygen, sulfur, selenium or substituted nitrogen N—$R^2$, N—O—$R^2$, in which $R^2$ can have the meanings given below, and $R^2$ is hydrogen,
alkyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
alkenyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
alkynyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
cycloalkyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
cycloalkenyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
(cycloalkyl)-(alkyl), optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
(cycloalkenyl)-(alkyl), optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
alkylcarbonyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
alkenylcarbonyl, optionally substituted by fluorine, chlorine or hydroxyl, alkoxy, oxo, phenyl;
(cycloalkyl)carbonyl, optionally substituted by fluorine, chlorine or hydroxyl, alkoxy, oxo, phenyl;
(cycloalkenyl)carbonyl, optionally substituted by fluorine, chlorine or hydroxyl, alkoxy, oxo, phenyl;
(cycloalkyl)-(alkyl)carbonyl, optionally substituted by fluorine, chlorine or hydroxyl, alkoxy, oxo, phenyl;
(cycloalkenyl)-(alkyl)carbonyl, optionally substituted by fluorine, chlorine or hydroxyl, alkoxy, oxo, phenyl;
alkyloxycarbonyl, optionally substituted by fluorine, chlorine, bromine, hydroxyl, alkoxy, alkylamino, dialkylamino, alkylthio;
alkenyloxycarbonyl, optionally substituted by fluorine, chlorine, hydroxyl, alkoxy, oxo, phenyl;
alkynyloxycarbonyl, optionally substituted by fluorine, chlorine, hydroxyl, alkoxy, oxo, phenyl;
alkylthiocarbonyl, optionally substituted by fluorine, chlorine, hydroxyl, alkoxy, oxo, phenyl;
alkenylthiocarbonyl, optionally substituted by fluorine, chlorine, hydroxyl, alkoxy, oxo, phenyl;
alkylamino- and dialkylaminocarbonyl, optionally substituted by fluorine, chlorine, hydroxyl, alkoxy, oxo, phenyl;
alkenylamino- and dialkenylaminocarbonyl, optionally substituted by fluorine, chlorine, hydroxyl, alkoxy, oxo, phenyl;

alkylsulfonyl, optionally substituted by fluorine, chlorine, hydroxyl, alkoxy, alkylthio, oxo, phenyl;

alkenylsulfonyl, optionally substituted by fluorine, chlorine, hydroxyl, alkoxy, oxo, phenyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl, arylalkoxycarbonyl, which is unsubstituted or substituted by up to five radicals $R^6$ which are independent of one another, where $R^6$ is as defined above;

or heteroaryl, heteroarylalkyl, heteroarylalkenyl, heteroarylalkylcarbonyl or heteroarylalkenylcarbonyl, which is substituted by up to three radicals $R^6$ which are independent of one another, and $R^3$ is hydrogen, alkyl, optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

alkenyl, optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkyl, optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkenyl, optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

or aryl, arylalkyl, heteroaryl or heteroarylalkyl, which is unsubstituted or substituted by up to five radicals $R^6$ which are independent of one another, where $R^6$ is as defined above, and $R^4$ is oxygen, sulfur, $NOR^2$, NOH, where $R^2$ is defined as indicated above, or $R^4$ is an alkyl radical bonded via a double bond, which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl or $R^4$ can be two hydrogen atoms residing on the linking carbon atom, where in this case additionally to the definitions indicated below for $R^5$ this radical can also be hydrogen or alkylcarbonyl, and in which m is 0 or 1, and $R^5$ is alkyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkenyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenyisulfonyl, oxo, thioxo, carboxyl, carbamoyl;

alkynyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkenyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

(cycloalkyl)-(alkyl), optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

(cycloalkenyl)-(alkyl), optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

or aryl, arylalkyl, arylalkenyl, arylalkynyl, which is unsubstituted or substituted by up to five radicals $R^6$ which are independent of one another, where $R^6$ is as defined above;

or heteroaryl, heteroarylalkyl, heteroarylalkenyl, which is unsubstituted or substituted by up to three radicals $R^6$ which are independent of one another, optical isomers thereof, diastereomers in pure form or in the form of mixtures thereof and addition salts and prodrugs thereof, with the exception of the compounds of the formula I in which the radicals $R^1$, $R^2$, $R^3$, $R^4$, $R^5$, X and m simultaneously have the following meanings:

$R^2$ is hydrogen, $R^3$ is phenyl, which is unsubstituted or substituted as indicated above, X is oxygen, $R^4$ is oxygen, m is 1 and $R^5$ is $C_1$–$C_6$-alkyl furthermore with the exception of the compounds of the formula I in which the radicals $R^2$, $R^3$, $R^4$, $R^5$, X and m simultaneously have the following meanings:

$R^2$ is hydrogen, $R^3$ is phenyl, which is unsubstituted or substituted as indicated above, X is oxygen, $R^4$ is oxygen, m is 0 and $R^5$ is as defined above furthermore with the exception of the compounds of the formula I in which $R^1$ and $R^2$ are hydrogen,
$R^3$ is hydrogen, methyl or ethyl,
$R^4$ is oxygen and
$R^5$ is methyl,
furthermore with the exception of the compounds of the formula I in which
$R^1$ is hydrogen,
$R^2$ is $C_1$–$C_4$-alkyl,
$R^3$ is phenyl (which is unsubstituted or substituted as indicated above),
$R^4$ is 0,
m is 1,
X is 0 and
$R^5$ is methyl, ethyl
furthermore with the exception of the compounds of the formula I in which
$R^1$ and $R^2$ are hydrogen,
$R^3$ is ethenyl,
$R^4$ is 0,
m is 1,
X is 0 and
$R^5$ is methyl, ethyl,
furthermore with the exception of the compounds of the formula Ia in which
$R^1$ and $R^2$ are hydrogen,
$R^3$ is ethyl,
$R^4$ is 0,
m is 1,
X is 0 and
$R^5$ is methyl.

In a preferred group of compounds of the formulae I and Ia:
II)
    n is zero, one, two, three,
    the individual substituents $R^1$ independently of one another are fluorine, chlorine, bromine, iodine, trifluoromethyl, trifluoromethoxy, hydroxyl, ($C_1$–$C_{10}$)-alkyl, ($C_3$–$C_8$)-cycloalkyl, ($C_1$–$C_{10}$)-alkoxy, ($C_1$–$C_{10}$)-alkoxy(($C_1$–$C_{10}$)-alkoxy), ($C_1$–$C_{10}$)-alkylthio, ($C_1$–$C_{10}$)-alkylsulfinyl, ($C_1$–$C_{10}$)-alkylsulfonyl, nitro, amino, azido, ($C_1$–$C_{10}$)-alkylamino, ($C_1$–$C_{10}$)-dialkylamino, piperidino, morpholino, 1-pyrrolidinyl, ($C_1$–$C_{10}$)-acyl, ($C_1$–$C_{10}$)-acyloxy, ($C_1$–$C_{10}$)-acylamino, cyano, carbamoyl, carboxyl, ($C_1$–$C_{10}$)-alkyloxycarbonyl, hydroxysulfonyl, sulfamoyl or
        a phenyl, phenoxy, phenoxycarbonyl, phenylthio, phenylsulfinyl, phenylsulfonyl, phenoxysulfonyl, phenylsulfonyloxy, phenylsulfonylamino, benzoyl, heteroaroyl, heteroaryl or heteroarylmethyl radical, which is optionally substituted by up to five radicals $R^6$ which are independent of one another,
    where $R^6$ can be
        fluorine, chlorine, bromine, iodine, cyano, trifluoromethyl, trifluoromethoxy, nitro, amino, azido, ($C_1$–$C_6$)-alkyl, ($C_3$–$C_8$)-cycloalkyl, ($C_1$–$C_6$)-alkoxy, ($C_1$–$C_6$)-alkylthio, ($C_1$–$C_6$)-alkylsulfinyl, ($C_1$–$C_6$)-alkylsulfonyl, ($C_1$–$C_6$)-alkylamino, ($C_1$–$C_6$)-dialkylamino, ($C_1$–$C_6$)-alkyloxycarbonyl, phenyl, phenoxy or heteroaryl,
    X is oxygen, sulfur or substituted nitrogen N—$R^2$, N—O—$R^2$, in which $R^2$ can have the meanings given below,
and $R^2$ is hydrogen,
    ($C_1$–$C_{12}$)-alkyl, optionally substituted by fluorine, chlorine, bromine, iodine, cyano, amino, mercapto, hydroxyl, ($C_1$–$C_6$)-acyloxy, benzoyloxy, benzyloxy, phenoxy, ($C_1$–$C_4$)-alkoxy, ($C_1$–$C_4$)-alkylamino, ($C_1$–$C_4$)-dialkylamino, ($C_1$–$C_4$)-alkylthio, ($C_1$–$C_4$)-alkylsulfonyl, phenylsulfonyl, oxo, carboxyl, carbamoyl;
    ($C_2$–$C_{12}$)-alkenyl, optionally substituted by fluorine, chlorine, bromine, iodine, cyano, amino, mercapto, hydroxyl, acyloxy, benzoyfoxy, benzyloxy, phenoxy, ($C_1$–$C_4$)-alkoxy, ($C_1$–$C_4$)-alkylamino, ($C_1$–$C_4$)-dialkylamino, ($C_1$–$C_4$)-alkylthio, ($C_1$–$C_4$)-alkylsulfonyl, phenylsulfonyl, oxo, thioxo, carboxyl, carbamoyl;
    ($C_2$–$C_8$)-alkynyl, optionally substituted by fluorine, chlorine, bromine, iodine, cyano, amino, mercapto, hydroxyl, acyloxy, benzoyloxy, benzyloxy, phenoxy, ($C_1$–$C_4$)-alkoxy, ($C_1$–$C_4$)-alkylamino, ($C_1$–$C_4$)-dialkylamino;
    ($C_1$–$C_6$)-alkylcarbonyl, optionally substituted by fluorine, chlorine, bromine, iodine, cyano, amino, mercapto, hydroxyl, ($C_1$–$C_4$)-acyloxy, benzoyloxy, benzyloxy, phenoxy, ($C_1$–$C_4$)-alkoxy, ($C_1$–$C_4$)-alkylamino, ($C_1$–$C_4$)-dialkylamino, ($C_1$–$C_4$)-alkylthio, ($C_1$–$C_4$)-alkylsulfonyl, phenylsulfonyl, oxo, thioxo, carboxyl, carbamoyl;
    ($C_2$–$C_6$)-alkenylcarbonyl, optionally substituted by fluorine, chlorine or hydroxyl, ($C_1$–$C_4$)-alkoxy, oxo, phenyl;
    ($C_3$–$C_6$)-(cycloalkyl)carbonyl, optionally substituted by fluorine, chlorine or hydroxyl, ($C_1$–$C_4$)-alkoxy, oxo, phenyl;
    ($C_3$–$C_6$)-(cycloalkenyl)carbonyl, optionally substituted by fluorine, chlorine or hydroxyl, ($C_1$–$C_4$)-alkoxy, oxo, phenyl;
    ($C_3$–$C_6$)-(cycloalkyl)-(($C_1$–$C_4$)-alkyl)carbonyl, optionally substituted by fluorine, chlorine or hydroxyl, ($C_1$–$C_4$)-alkoxy, oxo, phenyl;
    ($C_3$–$C_6$)-(cycloalkenyl)-(($C_1$–$C_4$)-alkyl)carbonyl, optionally substituted by fluorine, chlorine or hydroxyl, ($C_1$–$C_4$)-alkoxy, oxo, phenyl;
    ($C_1$–$C_6$)-alkyloxycarbonyl, optionally substituted by fluorine, chlorine, bromine, hydroxyl, ($C_1$–$C_4$)-alkoxy, ($C_1$–$C_4$)-alkylamino, ($C_1$–$C_4$)-dialkylamino, ($C_1$–$C_4$)-alkylthio;
    ($C_2$–$C_6$)-alkenyloxycarbonyl, optionally substituted by fluorine, chlorine, hydroxyl, ($C_1$–$C_4$)-alkoxy, oxo, phenyl;
    ($C_1$–$C_6$)-alkylamino- and ($C_1$–$C_6$)-dialkylaminocarbonyl, optionally substituted by fluorine, chlorine, hydroxyl, ($C_1$–$C_4$)-alkoxy, oxo, phenyl;
    or phenyl, phenylcarbonyl, phenyloxycarbonyl, phenylsulfonyl, phenyl-($C_1$–$C_2$)-alkyl, phenyl-($C_1$–$C_2$)-alkylcarbonyl, which is unsubstituted or substituted by up to five radicals $R^6$ which are independent of one another, where $R^6$ is as defined above;
    or heteroaryl, heteroaryl-($C_1$–$C_2$)-alkyl or heteroaryl-($C_1$–$C_2$)-alkylcarbonyl, which is substituted by up to two radicals $R^6$ which are independent of one another, and
$R^3$ is
    ($C_1$–$C_{15}$)-alkyl, optionally substituted by fluorine, chlorine, hydroxyl, amino, mercapto, ($C_1$–$C_6$)-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, $(C_1-C_6)$-alkylsulfinyl, carboxyl, carbamoyl;

$(C_2-C_{12})$-alkenyl, optionally substituted by fluorine, chlorine, hydroxyl, amino, mercapto, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, $(C_1-C_6)$-alkylsulfinyl, carboxyl, carbamoyl;

$(C_3-C_8)$-cycloalkyl, optionally substituted by fluorine, chlorine, hydroxyl, amino, mercapto, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, $(C_1-C_6)$-alkylsulfinyl, carboxyl, carbamoyl;

$(C_3-C_8)$-cycloalkenyl, optionally substituted by fluorine, chlorine, hydroxyl, amino, mercapto, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, $(C_1-C_6)$-alkylsulfinyl, carboxyl, carbamoyl;

or aryl, aryl-$(C_1-C_4)$-alkyl, heteroaryl or heteroaryl-$(C_1-C_4)$-alkyl, which is unsubstituted or substituted by up to five radicals $R^6$ which are independent of one another, where $R^6$ is as defined above, and $R^4$ is oxygen, $NOR^2$, NOH, where $R^2$ is defined as indicated above, or $R^4$ is a $(C_1-C_{10})$-alkyl radical bonded via a double bond, which is optionally substituted by fluorine, chlorine, hydroxyl, amino, mercapto, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, $(C_1-C_4)$-alkylsulfinyl, carboxyl, carbamoyl;

and m is 0 or 1, and $R^5$ is $(C_1-C_{15})$-alkyl, optionally substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

$(C_2-C_{12})$-alkenyl, optionally substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkytsulfonyl, phenylsulfonyl, oxo, thioxo, carboxyl, carbamoyl;

$(C_2-C_{10})$-alkynyl, optionally substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

$(C_3-C_{10})$-cycloalkyl, optionally substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

$(C_3-C_{10})$-cycloalkenyl, optionally substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

$(C_3-C_{10})$-(cycloalkyl)-($(C_1-C_4)$-alkyl), optionally substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

$(C_3-C_{10})$-(cycloalkenyl)-$(C_1-C_4)$-(alkyl), optionally substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

or aryl, aryl-$(C_1-C_4)$-alkyl, aryl-$(C_2-C_4)$-alkenyl, aryl-$(C_2-C_4)$-alkynyl, which is unsubstituted or substituted by up to five radicals $R^6$ which are independent of one another, where $R^6$ is as defined above;

or heteroaryl, heteroaryl-$(C_1-C_4)$-alkyl, which is unsubstituted or substituted by up to three radicals $R^6$ which are independent of one another, optical isomers thereof, diastereomers in pure form or in the form of mixtures thereof and addition salts and prodrugs thereof.

In a preferred group of compounds of the formulae I and Ia:

III)

n is zero, one, two, the individual substituents $R^1$ independently of one another are fluorine, chlorine, bromine, iodine, trifluoromethyl, trifluoromethoxy, hydroxyl, $(C_1-C_8)$-alkyl, $(C_3-C_8)$-cycloalkyl, $(C_1-C_8)$-alkoxy, $(C_1-C_8)$-alkoxy($(C_1-C_8)$-alkoxy), $(C_1-C_8)$-alkylthio, $(C_1-C_8)$-alkylsulfinyl, $(C_1-C_8)$-alkylsulfonyl, nitro, amino, azido, $(C_1-C_8)$-acyl, $(C_1-C_8)$-acyloxy, cyano, carbamoyl, carboxyl, $(C_1-C_8)$-alkyloxycarbonyl, sulfamoyl or a phenyl, phenoxy, phenoxycarbonyl, phenylthio, phenylsulfinyl, phenylsulfonyl, phenoxysulfonyl, phenylsulfonyloxy, phenylsulfonylamino or benzoyl radical, which is optionally substituted by up to two radicals $R^6$ which are independent of one another, where $R^6$ can be fluorine, chlorine, bromine, iodine, cyano, trifluoromethyl, trifluoromethoxy, nitro, amino, azido, $(C_1-C_4)$-alkyl, $(C_3-C_6)$-cycloalkyl, $(C_1-C_4)$-alkoxy, $(C_1-C_4)$-alkylthio, $(C_1-C_4)$-alkylsulfinyl, $(C_1-C_4)$-alkylsulfonyl, X is oxygen, sulfur or substituted nitrogen $N—R^2$, $N—O—R^2$, in which $R^2$ can have the meanings given below, and $R^2$ is hydrogen, $(C_1-C_8)$-alkyl, optionally substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, carboxyl, carbamoyl;

$(C_2-C_8)$-alkenyl, optionally substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl; and $R^3$ is
- $(C_1-C_{10})$-alkyl, optionally substituted by fluorine, chlorine, hydroxyl, amino, mercapto, $(C_1-C_6)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, $(C_1-C_4)$-alkylsulfinyl, carboxyl, carbamoyl;
- $(C_2-C_8)$-alkenyl, optionally substituted by fluorine, chlorine, hydroxyl, amino, mercapto, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, $(C_1-C_4)$-alkylsulfinyl, carboxyl, carbamoyl;
- $(C_3-C_8)$-cycloalkyl, optionally substituted by fluorine, chlorine, hydroxyl, amino, mercapto, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, $(C_1-C_4)$-alkylsulfinyl, carboxyl, carbamoyl;
- $(C_3-C_6)$-cycloalkenyl, optionally substituted by fluorine, chlorine, hydroxyl, amino, mercapto, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, $(C_1-C_4)$-alkylsulfinyl, carboxyl, carbamoyl;
- or aryl, aryl-$(C_1-C_2)$-alkyl, heteroaryl or heteroaryl-$(C_2-C_4)$-alkyl, which is unsubstituted or substituted by up to two radicals $R^6$ which are independent of one another, where $R^6$ is as defined above, and $R^4$ is oxygen,
and m is 0 or 1,
and $R^5$ is
- $(C_1-C_{10})$-alkyl, optionally substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_2-C_{10})$-alkenyl, optionally substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_2-C_8)$-alkynyl, optionally substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_3-C_8)$-cycloalkyl, optionally substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_3-C_8)$-cycloalkenyl, optionally substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_3-C_8)$-(cycloalkyl)-($(C_1-C_3)$-alkyl), optionally substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_3-C_8)$-(cycloalkenyl)-($(C_1-C_3)$-alkyl), optionally substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- or aryl, aryl-$(C_1-C_4)$-alkyl, aryl-$(C_2-C_4)$-alkenyl, aryl-$(C_1-C_4)$-alkynyl, which is unsubstituted or substituted by up to two radicals $R^6$ which are independent of one another, where $R^6$ is as defined above;
- or heteroaryl, heteroaryl-$(C_1-C_4)$-alkyl, which is unsubstituted or substituted by up to three radicals $R^6$ which are independent of one another,
- optical isomers thereof, diastereomers in pure form or in the form of their mixtures and addition salts and prodrugs thereof.

In a preferred group of compounds of the formulae I and Ia:

IV)
n is zero, one, two,
the individual substituents $R^1$ independently of one another are fluorine, chlorine, bromine, trifluoromethyl, trifluoromethoxy, $(C_1-C_6)$-alkyl, $(C_3-C_6)$-cycloalkyl, $(C_1-C_6)$-alkoxy, $(C_1-C_6)$-alkoxy($(C_1-C_6)$-alkoxy), $(C_1-C_6)$-alkylthio, $(C_1-C_6)$-alkylsulfinyl, $(C_1-C_6)$-acyl, $(C_1-C_6)$-acyloxy, carboxyl, $(C_1-C_6)$-alkyloxycarbonyl, or
a phenyl, phenoxy, phenoxycarbonyl, phenylthio, phenylsulfonyl, phenoxysulfonyl, phenylsulfonyloxy, phenylsulfonylamino or benzoyl radical, which is optionally substituted by up to two radicals $R^6$ which are independent of one another,
where $R^6$ can be
fluorine, chlorine, bromine, trifluoromethyl, trifluoromethoxy, azido, $(C_1-C_4)$-alkyl, $(C_4-C_6)$-cycloalkyl, $(C_1-C_4)$-alkoxy, $(C_1-C_4)$-alkylthio,
X is oxygen, sulfur or substituted nitrogen N—$R^2$, N—O—$R^2$, in which $R^2$ can have the meanings given below,
and $R^2$ is hydrogen, $(C_1-C_4)$-alkyl, optionally substituted by fluorine, chlorine, bromine, $(C_1-C_3)$- acyloxy, benzoyloxy, benzyloxy, phenoxy, $(C_1-C_3)$-alkoxy, phenylsulfonyl, oxo, carboxyl, carbamoyl;

$(C_2-C_6)$-alkenyl, optionally substituted by fluorine, chlorine, bromine, $(C_1-C_3)$-acyloxy, benzoyloxy, benzyloxy, phenoxy, $(C_1-C_3)$-alkoxy, phenylsulfonyl, oxo, carboxyl, carbamoyl; and $R^3$ is $(C_1-C_8)$-alkyl, optionally substituted by fluorine, chlorine, hydroxyl, amino, $(C_1-C_4)$-acyloxy, benzoyloxy, benzyloxy, phenoxy, $(C_1-C_4)$-alkoxy, carboxyl;

$(C_2-C_6)$-alkenyl, optionally substituted by fluorine, chlorine, hydroxyl, amino, $(C_1-C_4)$-acyloxy, benzoyloxy, benzyloxy, phenoxy, $(C_1-C_4)$-alkoxy, carboxyl;

$(C_3-C_6)$-cycloalkyl, optionally substituted by fluorine, chlorine, hydroxyl, amino, $(C_1-C_4)$-acyloxy, benzoyloxy, benzyloxy, phenoxy, $(C_1-C_4)$-alkoxy, carboxyl;

$(C_3-C_6)$-cycloalkenyl, optionally substituted by fluorine, chlorine, hydroxyl, amino, $(C_1-C_4)$-acyloxy, benzoyloxy, benzyloxy, phenoxy, $(C_1-C_4)$-alkoxy, carboxyl;

or aryl, aryl-$(C_1-C_2)$-alkyl, which is unsubstituted or substituted by up to two radicals $R^6$ which are independent of one another, where $R^6$ is as defined above, and $R^4$ is oxygen, and m is 0 or 1, and $R^5$ is $(C_1-C_8)$-alkyl, optionally substituted by fluorine, chlorine, bromine, cyano, amino, hydroxyl, $(C_1-C_4)$-acyloxy, benzoyloxy, benzyloxy, phenoxy, $(C_1-C_4)$-alkoxy, oxo, carboxyl, carbamoyl;

$(C_2-C_8)$-alkenyl, optionally substituted by fluorine, chlorine, bromine, iodine, cyano, amino, hydroxyl, $(C_1-C_4)$-acyloxy, benzoyloxy, benzyloxy, phenoxy, $(C_1-C_4)$-alkoxy, oxo, carboxyl, carbamoyl;

$(C_2-C_6)$-alkynyl, optionally substituted by fluorine, chlorine, bromine, cyano, amino, hydroxyl, $(C_1-C_4)$-acyloxy, benzoyloxy, benzyloxy, phenoxy, $(C_1-C_4)$-alkoxy, oxo, carboxyl, carbamoyl;

$(C_3-C_6)$-cycloalkyl, optionally substituted by fluorine, chlorine, bromine, cyano, amino, hydroxyl, $(C_1-C_4)$-acyloxy, benzoyloxy, benzyloxy, phenoxy, $(C_1-C_4)$-alkoxy, oxo, carboxyl, carbamoyl;

$(C_3-C_6)$-cycloalkenyl, optionally substituted by fluorine, chlorine, bromine, amino, hydroxyl, $(C_1-C_4)$-acyloxy, benzoyloxy, benzyloxy, phenoxy, $(C_1-C_4)$-alkoxy;

$(C_3-C_6)$-(cycloalkyl)-$((C_1-C_2)$-alkyl), optionally substituted by fluorine, chlorine, bromine, amino, hydroxyl, $(C_1-C_4)$-acyloxy, benzoyloxy, benzyloxy, phenoxy;

$(C_3-C_6)$-(cycloalkenyl)-$((C_1-C_2)$-alkyl), optionally substituted by fluorine, chlorine, bromine, amino, hydroxyl, $(C_1-C_4)$-acyloxy, benzoyloxy, benzyloxy, phenoxy;

or aryl, aryl-$(C_1-C_4)$-alkyl, aryl-$(C_2-C_4)$-alkenyl, which is unsubstituted or substituted by up to two radicals $R^6$ which are independent of one another, where $R^6$ is as defined above;

or heteroaryl, heteroaryl-$(C_1-C_4)$-alkyl, which is unsubstituted or substituted by up to three radicals $R^6$ which are independent of one another, optical isomers thereof, diastereomers in pure form or in the form of mixtures thereof and addition salts and prodrugs thereof.

In a preferred group of compounds of the formulae I and Ia:

V)

n is zero, one, the substituent $R^1$ is fluorine, chlorine, bromine, trifluoromethyl, trifluoromethoxy, $(C_5-C_6)$-cycloalkyl, $(C_1-C_4)$-alkoxy, $(C_1-C_4)$-alkoxy$((C_1-C_4)$-alkoxy), $(C_1-C_4)$-alkylthio, $(C_1-C_4)$-acyl, or a phenyl, phenoxy- or benzoyl radical optionally substituted by a radical $R^6$, where $R^6$ can be fluorine, chlorine, bromine, trifluoromethyl, trifluoromethoxy, $(C_1-C_4)$-alkyl, $(C_1-C_4)$-alkoxy, $(C_1-C_4)$-alkylthio, X is oxygen or sulfur, and $R^2$ is hydrogen, and $R^3$ is $(C_1-C_6)$-alkyl;

$(C_2-C_6)$-alkenyl;

$(C_3-C_6)$-cycloalkyl;

or phenyl, benzyl, which is unsubstituted or substituted by up to 2 radicals $R^6$ which are independent of one another, where $R^6$ is as defined above, and $R^4$ is oxygen, and m is 1, and $R^5$ is $(C_1-C_6)$-alkyl, optionally substituted by fluorine, chlorine, bromine, cyano, amino, hydroxyl, $(C_1-C_4)$-acyloxy, benzoyloxy, benzyloxy, phenoxy, $(C_1-C_4)$-alkoxy;

$(C_2-C_6)$-alkenyl, optionally substituted by fluorine, chlorine, bromine, amino, hydroxyl, $(C_1-C_4)$-acyloxy, carboxyl;

$(C_3-C_6)$-cycloalkyl;

$(C_3-C_6)$-cycloalkenyl;

$(C_3-C_6)$-(cycloalkyl)-$((C_1-C_2)$-alkyl);

or aryl, aryl-$(C_1-C_4)$-alkyl, which is unsubstituted or substituted by up to two radicals $R^6$ which are independent of one another, where $R^6$ is as defined above;

optical isomers thereof, diastereomers in pure form or in the form of mixtures thereof and addition salts and prodrugs thereof.

VI) Very particularly preferred compounds are those mentioned by way of example and listed in the following Table T1:

TABLE T1

Examples of very particularly preferred compounds

| Compound number | n | $R^1$ | $R^2$ | $R^3$ | $R^4$ | $(O)_m$-$R^5$ | X |
|---|---|---|---|---|---|---|---|
| a.1 | 1 | 6-Cl | H | methyl | O | O-ethyl | O |
| a.2 | 1 | 6-Cl | H | methyl | O | O-ethyl | S |
| a.3 | 1 | 6-Cl | H | methyl | O | O-ethyl | NOH |
| a.4 | 1 | 6-Cl | H | methyl | O | O-isopropyl | O |
| a.5 | 1 | 6-Cl | H | methyl | O | O-isopropyl | S |
| a.6 | 1 | 6-Cl | H | methyl | O | O-isopropyl | NOH |
| a.7 | 1 | 6-OMe | H | methyl | O | O-ethyl | O |

TABLE T1-continued

Examples of very particularly preferred compounds

| Compound number | n | $R^1$ | $R^2$ | $R^3$ | $R^4$ | $(O)_m$-$R^5$ | X |
|---|---|---|---|---|---|---|---|
| a.8 | 1 | 6-OMe | H | methyl | O | O-ethyl | S |
| a.9 | 1 | 6-OMe | H | methyl | O | O-ethyl | NOH |
| a.10 | 1 | 6-OMe | H | methyl | O | O-isopropyl | O |
| a.11 | 1 | 6-OMe | H | methyl | O | O-isopropyl | S |
| a.12 | 1 | 6-OMe | H | methyl | O | O-isopropyl | NOH |
| a.13 | 1 | F | H | methyl | O | O-ethyl | O |
| a.14 | 1 | F | H | methyl | O | O-ethyl | S |
| a.15 | 1 | F | H | methyl | O | O-ethyl | NOH |
| a.16 | 1 | F | H | methyl | O | O-isopropyl | O |
| a.17 | 1 | F | H | methyl | O | O-isopropyl | S |
| a.18 | 1 | F | H | methyl | O | O-isopropyl | NOH |
| a.19 | 1 | 6-Cl | H | ethyl | O | O-ethyl | O |
| a.20 | 1 | 6-Cl | H | ethyl | O | O-ethyl | S |
| a.21 | 1 | 6-OMe | H | ethyl | O | O-ethyl | O |
| a.22 | 1 | 6-OMe | H | ethyl | O | O-ethyl | S |
| a.23 | 1 | F | H | ethyl | O | O-ethyl | O |
| a.24 | 1 | F | H | ethyl | O | O-ethyl | S |
| a.25 | 1 | 6-Cl | H | ethyl | O | O-isopropyl | O |
| a.26 | 1 | 6-Cl | H | ethyl | O | O-isopropyl | S |
| a.27 | 1 | 6-OMe | H | ethyl | O | O-isopropyl | O |
| a.28 | 1 | 6-OMe | H | ethyl | O | O-isopropyl | S |
| a.29 | 1 | F | H | ethyl | O | O-isopropyl | O |
| a.30 | 1 | F | H | ethyl | O | O-isopropyl | S |
| a.31 | 1 | 6-Cl | H | isopropyl | O | O-ethyl | O |
| a.32 | 1 | 6-Cl | H | isopropyl | O | O-ethyl | S |
| a.33 | 1 | 6-OMe | H | isopropyl | O | O-ethyl | O |
| a.34 | 1 | 6-OMe | H | isopropyl | O | O-ethyl | S |
| a.35 | 1 | F | H | isopropyl | O | O-ethyl | O |
| a.36 | 1 | F | H | isopropyl | O | O-ethyl | S |
| a.37 | 1 | 6-Cl | H | isopropyl | O | O-isopropyl | O |
| a.38 | 1 | 6-Cl | H | isopropyl | O | O-isopropyl | S |
| a.39 | 1 | 6-OMe | H | isopropyl | O | O-isopropyl | O |
| a.40 | 1 | 6-OMe | H | isopropyl | O | O-isopropyl | S |
| a.41 | 1 | F | H | isopropyl | O | O-isopropyl | O |
| a.42 | 1 | F | H | isopropyl | O | O-isopropyl | S |
| a.43 | 1 | 6-Cl | H | phenyl | O | O-ethyl | O |
| a.44 | 1 | 6-Cl | H | phenyl | O | O-ethyl | S |
| a.45 | 1 | 6-OMe | H | phenyl | O | O-ethyl | O |
| a.46 | 1 | 6-OMe | H | phenyl | O | O-ethyl | S |
| a.47 | 1 | F | H | phenyl | O | O-ethyl | O |
| a.48 | 1 | F | H | phenyl | O | O-ethyl | S |
| a.49 | 1 | 6-Cl | H | phenyl | O | O-isopropyl | O |
| a.50 | 1 | 6-Cl | H | phenyl | O | O-isopropyl | S |
| a.51 | 1 | 6-OMe | H | phenyl | O | O-isopropyl | O |
| a.52 | 1 | 6-OMe | H | phenyl | O | O-isopropyl | S |
| a.53 | 1 | F | H | propyl | O | O-isopropyl | O |
| a.54 | 1 | F | H | propyl | O | O-isopropyl | S |
| a.55 | 1 | 6-Cl | H | propyl | O | O-ethyl | O |
| a.56 | 1 | 6-Cl | H | propyl | O | O-ethyl | S |
| a.57 | 1 | 6-OMe | H | propyl | O | O-ethyl | O |
| a.58 | 1 | 6-OMe | H | propyl | O | O-ethyl | S |
| a.59 | 1 | F | H | propyl | O | O-ethyl | O |
| a.60 | 1 | F | H | propyl | O | O-ethyl | S |
| a.61 | 1 | 6-Cl | H | propyl | O | O-isopropyl | O |
| a.62 | 1 | 6-Cl | H | propyl | O | O-isopropyl | S |
| a.63 | 1 | 6-OMe | H | propyl | O | O-isopropyl | O |
| a.64 | 1 | 6-OMe | H | propyl | O | O-isopropyl | S |
| a.65 | 1 | F | H | propyl | O | O-isopropyl | O |
| a.66 | 1 | F | H | propyl | O | O-isopropyl | S |
| a.67 | 1 | 6-Cl | H | n-butyl | O | O-ethyl | O |
| a.68 | 1 | 6-Cl | H | n-butyl | O | O-ethyl | S |
| a.69 | 1 | 6-OMe | H | n-butyl | O | O-ethyl | O |
| a.70 | 1 | 6-OMe | H | n-butyl | O | O-ethyl | S |
| a.71 | 1 | F | H | n-butyl | O | O-ethyl | O |
| a.72 | 1 | F | H | n-butyl | O | O-ethyl | S |
| a.73 | 1 | 6-Cl | H | n-butyl | O | O-isopropyl | O |
| a.74 | 1 | 6-Cl | H | n-butyl | O | O-isopropyl | S |
| a.75 | 1 | 6-OMe | H | n-butyl | O | O-isopropyl | O |
| a.76 | 1 | 6-OMe | H | n-butyl | O | O-isopropyl | S |
| a.77 | 1 | F | H | n-butyl | O | O-isopropyl | O |
| a.78 | 1 | F | H | n-butyl | O | O-isopropyl | S |
| a.79 | 1 | H | H | methyl | O | O-isopropyl | O |
| a.80 | 1 | H | H | methyl | O | O-isopropyl | S |
| a.81 | 1 | H | H | ethyl | O | O-isopropyl | O |
| a.82 | 1 | H | H | ethyl | O | O-isopropyl | S |
| a.83 | 1 | H | H | isopropyl | O | O-isopropyl | O |
| a.84 | 1 | H | H | isopropyl | O | O-isopropyl | S |
| a.85 | 1 | H | H | methyl | O | O-ethyl | O |
| a.86 | 1 | H | H | methyl | O | O-ethyl | S |
| a.87 | 1 | H | H | ethyl | O | O-ethyl | O |
| a.88 | 1 | H | H | ethyl | O | O-ethyl | S |
| a.89 | 1 | H | H | isopropyl | O | O-ethyl | O |
| a.90 | 1 | H | H | isopropyl | O | O-ethyl | S |

Preferred compounds of the formula I are furthermore those in which at least one of the substituents independently of one another has the following meaning:

n is zero or one;

the substituent $R^1$ is fluorine, chlorine, bromine, trifluoromethoxy, methoxy, ethoxy, propoxy, butoxy, methylthio, ethylthio, propylthio, butylthio, methoxymethoxy, methoxyethoxy, acetyl, propionyl, or a phenyl, phenoxy or benzoyl radical, which is optionally substituted by a radical $R^6$, where $R^6$ can be fluorine, chlorine, bromine, trifluormethyl, trifluoromethoxy, methyl, ethyl, propyl, methoxy, ethoxy, propoxy, methylthio or ethylthio;

X is oxygen or sulfur;

$R^2$ is hydrogen;

$R^3$ is methyl, ethyl, propyl, butyl, pentyl or hexyl, ethenyl, propenyl, butenyl, pentenyl, hexenyl, cyclopropyl, cyclobutyl, cyclopentyl, cyclohexyl;

$R^3$ is phenyl or benzyl, which is unsubstituted or substituted by up to two radicals $R^6$ which are independent of one another, where $R^6$ is as defined above;

$R^4$ is oxygen or sulfur;

m is zero or one; and $R^5$ is methyl, ethyl, propyl, butyl, pentyl, hexyl, ethenyl, propenyl, butenyl, pentenyl, hexenyl, cyclopropyl, cyclobutyl, cyclopentyl, cyclohexyl, cyclopropylmethyl, cyclobutylmethyl, cyclopentylmethyl, cyclohexylmethyl, or $R^5$ is phenyl, benzyl, phenylethyl, which is unsubstituted or substituted by up to two radicals $R^6$ which are independent of one another, where $R^6$ is as defined above.

The invention furthermore relates to the use of compounds of the formulae I' and I'a for the production of pharmaceuticals for the treatment or prophylaxis of retroviral disorders such as, for example, AIDS,

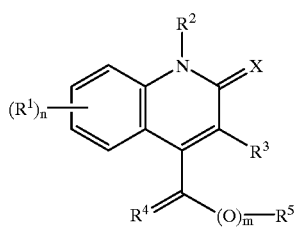

and their tautomeric forms, of the formula I'a,

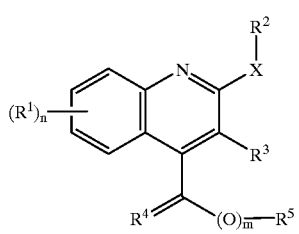

in which
n is zero, one, two, three or four,
the individual substituents $R^1$ independently of one another are fluorine, chlorine, bromine, iodine, trifluoromethyl, trifluoromethoxy, hydroxyl, alkyl, cycloalkyl, alkoxy, alkoxy(alkoxy), alkylthio, alkylsulfinyl, alkylsulfonyl, nitro, amino, azido, alkylamino, dialkylamino, piperidino, morpholino, 1-pyrrolidinyl, acyl, acyloxy, acylamino, cyano, carbamoyl, carboxyl, alkyloxycarbonyl, hydroxysulfonyl, sulfamoyl or
  a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, heteroaroyl, heteroaryl or heteroarylmethyl radical, which is optionally substituted by up to five radicals $R^6$ which are independent of one another,
where $R^6$ can be
  fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, alkyloxycarbonyl, phenyl, phenoxy or heteroaryl,
X is oxygen, sulfur, selenium or substituted nitrogen N—$R^2$, N—O—$R^2$, in which $R^2$ can have the meanings given below,
and $R^2$ is hydrogen,
  alkyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
  alkenyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
  alkynyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
  cycloalkyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
  cycloalkenyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
  (cycloalkyl)-(alkyl), optionally substituted by fluorine, chlorine, bromine, iodine, cyano, amino, mercapto, hydroxyl, acyloxy, benzoyloxy, benzyioxy, phenoxy, alkoxy, alkylamino, dialkylamino, alkylthio, alkylsulfonyl, phenylsulfonyl, oxo, thioxo, carboxyl, carbamoyl;
  (cycloalkenyl)-(alkyl), optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
  alkylcarbonyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
  alkenylcarbonyl, optionally substituted by fluorine, chlorine or hydroxyl, alkoxy, oxo, phenyl;
  (cycloalkyl)carbonyl, optionally substituted by fluorine, chlorine or hydroxyl, alkoxy, oxo, phenyl;
  (cycloalkenyl)carbonyl, optionally substituted by fluorine, chlorine or hydroxyl, alkoxy, oxo, phenyl;
  (cycloalkyl)-(alkyl)carbonyl, optionally substituted by fluorine, chlorine or hydroxyl, alkoxy, oxo, phenyl;
  (cycloalkenyl)-(alkyl)carbonyl, optionally substituted by fluorine, chlorine or hydroxyl, alkoxy, oxo, phenyl;
  alkyloxycarbonyl, optionally substituted by fluorine, chlorine, bromine, hydroxyl, alkoxy, alkylamino, dialkylamino, alkylthio;
  alkenyloxycarbonyl, optionally substituted by fluorine, chlorine, hydroxyl, alkoxy, oxo, phenyl;
  alkynyloxycarbonyl, optionally substituted by fluorine, chlorine, hydroxyl, alkoxy, oxo, phenyl;
  alkylthiocarbonyl, optionally substituted by fluorine, chlorine, hydroxyl, alkoxy, oxo, phenyl;
  alkenylthiocarbonyl, optionally substituted by fluorine, chlorine, hydroxyl, alkoxy, oxo, phenyl;
  alkylamino and dialkylaminocarbonyl, optionally substituted by fluorine, chlorine, hydroxyl, alkoxy, oxo, phenyl;
  alkenylamino and dialkenylaminocarbonyl, optionally substituted by fluorine, chlorine, hydroxyl, alkoxy, oxo, phenyl;
  alkylsulfonyl, optionally substituted by fluorine, chlorine, hydroxyl, alkoxy, alkylthio, oxo, phenyl;

alkenylsulfonyl, optionally substituted by fluorine, chlorine, hydroxyl, alkoxy, oxo, phenyl;

aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl, arylalkoxycarbonyl, which is substituted by up to five radicals $R^6$ which are independent of one another, where $R^6$ is as defined above;

or heteroaryl, heteroarylalkyl, heteroarylalkenyl, heteroarylalkylcarbonyl or heteroarylalkenylcarbonyl, which is substituted by up to three radicals $R^6$ which are independent of one another, and $R^3$ is hydrogen, cyano, alkyl, optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

alkyloxy, optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

alkenyl, optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkyl, optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkenyl, optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

or aryl, arylalkyl, heteroaryl or heteroarylalkyl, which is substituted by up to five radicals $R^6$ which are independent of one another, where $R^6$ is as defined above, and $R^4$ is oxygen, sulfur, $NOR^2$, NOH, where $R^2$ is defined as indicated above, or $R^4$ is an aryl radical bonded via a double bond, which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl or $R^4$ can be two hydrogen atoms residing on the linking carbon atom, where in this case additionally to the definitions indicated below for $R^5$ this radical can also be alkylcarbonyl, and in which m is 0 or 1, and $R^5$ is hydrogen, alkyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkenyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkynyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkenyl, optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkyl)-(alkyl), optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

(cycloalkenyl)-(alkyl), optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

or aryl, arylalkyl, arylalkenyl, arylalkynyl, which is substituted by up to five radicals $R^6$ which are independent of one another, where $R^6$ is as defined above;

or heteroaryl, heteroarylalkyl, heteroarylalkenyl, which is substituted by up to three radicals $R^6$ which are independent of one another, optical isomers thereof, diastereomers thereof in pure form or in the form of mixtures thereof and addition salts and prodrugs thereof.

The compounds mentioned under I) to VI) are preferred.

The alkyl groups mentioned in the preceding definitions can be straight-chain or branched. If not defined otherwise, they preferably contain 1–8, particularly preferably 1–6, in particular 1–4 carbon atoms. Examples are the methyl, ethyl, propyl, 1-methylethyl, butyl, 1-methylpropyl, 2-methylpropyl, 1,1-dimethylethyl group and the like.

The alkyl radicals of dialkylamino groups can be identical or different and are defined, in particular, as indicated above. The details of the number of carbon atoms in the dialkyl compounds always relate only to one of the alkyl radicals.

The alkenyl groups mentioned in the preceding definitions can be straight-chain or branched and contain 1 to 3 double bonds. If not defined otherwise, these groups preferably contain 2–8, in particular 2–6 carbon atoms. Examples are the 2-propenyl, 1-methylethenyl, 2-butenyl, 3-butenyl, 2-methyl-2-propenyl, 3-methyl-2-butenyl, 2,3-dimethyl-2-butenyl, 3,3-dichloro-2-propenyl and pentadienyl group and the like.

The alkynyl groups mentioned in the preceding definitions can be straight-chain or branched and contain 1 to 3 triple bonds. If not defined otherwise, they preferably contain 2–8, particularly preferably 3–6 carbon atoms. Examples are the 2-propynyl and 3-butynyl group and the like.

The cycloalkyl and cycloalkenyl groups mentioned in the preceding definitions contain, if not defined otherwise, preferably 3–8, particularly preferably 4–6 carbon atoms. Examples are the cyclopropyl, cyclobutyl, cyclopentyl, cyclopentenyl, cyclohexyl or cyclohexenyl group.

The acyl groups mentioned in the preceding definitions can be aliphatic, cycloaliphatic or aromatic. If not defined otherwise, they preferably contain 1–8, particularly preferably 2–7 carbon atoms. Exemplary acyl groups are the formyl, acetyl, chloroacetyl, trifluoroacetyl, hydroxyacetyl, glycyl, propionyl, butyryl, Isobutyryl, pivaloyl, cyclohexanoyl or benzoyl group.

For the aryl groups mentioned in the preceding definitions, aromatic groups having 6–14 carbon atoms are preferably suitable, in particular having 6–10 carbon atoms, such as, for example, phenyl and naphthyl.

In the abovementioned heterocyclic rings and heteroaryl groups, suitable heteroatoms are, in particular, for example O, S, and N, where if a saturated N-containing ring N—Z is present in this position Z is H or $R^2$ having the respective definitions described above.

If not defined otherwise, the heterocyclic rings preferably have 1–15 carbon atoms and 1–6 heteroatoms, in particular 3–11 carbon atoms and 1–4 heteroatoms.

Possible heterocyclic rings or heteroaryl groups mentioned in the preceding definitions are, for example, thiophene, furan, pyridine, pyrimidine, indole, quinoline, isoquinoline, oxazole, isoxazole, thiazole or isothiazole.

In the same manner, these definitions apply to heteroaryl in the heteroarylmethyl radical. The aralkyl groups mentioned in the preceding definitions are, for example, benzyl, phenylethyl, naphthylmethyl or styryl.

The abovementioned substituents R1 to R6 are preferably substituted 3 times, particularly preferably 2 times, in particular one time by the substituents indicated in each case.

For the respective summarized substituent definitions (such as, for example, arylalkoxycarbonyl), the ranges described beforehand as preferred for the individual substituents are likewise preferred.

Depending on the various substituents, compounds of the formulae I and Ia can have several asymmetric carbon atoms. The invention therefore relates both to the pure stereoisomers and to mixtures thereof, such as, for example, the associated racemate.

The pure stereoisomers of the compounds of the formulae I and Ia can be prepared directly by known methods or in analogy to known methods or subsequently separated.

The present invention furthermore includes processes for the preparation of compounds of the formulae I and Ia as explained above under I) to VI), which comprise A) for the preparation of compounds of the formula I or Ia in which X and $R^4$ are oxygen, m is 0 or 1, with the other radicals as defined above under I) to VI), reacting a compound of the formula II where A is a leaving group, preferably a halogen atom, with a compound of the formula III where m is hydrogen, a metal atom or a metal atom equivalent, preferably an alkali metal or alkaline earth metal,

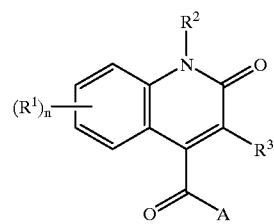

II

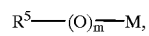

III or

B) reacting compounds of the formula I where X is oxygen, and $R^1$ to $R^5$ are as defined above, with a sulfurizing reagent to give compounds of the formula I where X is sulfur and $R^1$ to $R^5$ are as defined above, or C) reacting a compound of the formula I where $R^1$–$R^5$ are as defined under I) to VI) and X is an oxygen or sulfur atom, with a compound of the formula IV or IVa

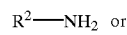 (IV)

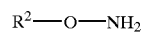 (IVa)

to give derivatives of the formula I where $R^1$–$R^5$ are as defined under I) to VI) and X is N—$R^2$ or N—O—$R^2$ or D) reacting a compound of the formula II where A is chlorine and $R^1$ to $R^5$ are as defined above, with a reductant to give compounds of the formula I where $R^1$ to $R^3$ are as defined above, $R^4$ together with the linking carbon atom forming a $CH_2$ group and $(O)_m$—$R^5$ being hydroxyl,

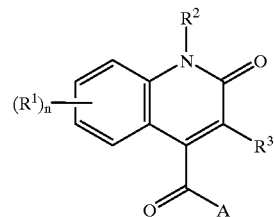

II or

E) reacting a compound of the formula I or Ia where $R^2$ is hydrogen and $R^1$, $R^3$, $R^4$ and $R^5$ are as defined under I to VI, with a compound of the formula V
where B is a leaving group, to give derivatives of the formula I in which the definitions described in I) to VI) for the compounds of the formulae I and Ia apply to $R^2$ with the exception of $R^2$ is hydrogen, and where groups can optionally be converted into functional groups mentioned under I–VI according to prior art processes.

The abovementioned method A preferably proceeds under the following conditions:

The reaction preferably proceeds using a 0.2 to 10-fold excess of the reaction component III. The reaction is expediently carried out in an organic solvent or a solvent mixture, at −78° C. to 150° C., preferably at the boiling temperature of the reaction mixture and if possible under anhydrous conditions.

Suitable solvents are, for example, aromatic hydrocarbons such as toluene, xylene, ethers such as tetrahydrofuran or glycol dimethyl ether or mixtures of these solvents, and furthermore for compounds where m=1, the alcohol corresponding to the compound of the formula III (M is hydrogen).

The abovementioned method B preferably proceeds under the following conditions:

For the reaction as described beforehand under B), the following is preferably used as a sulfurizing reagent 2,4-bis (4-methoxyphenyl)-1,3-dithia-2,4-diphosphetane-2,4-disulfide (Lawesson's reagent), bis(tricyclohexyltin) sulfide, bis(tri-n-butyltin) sulfide, bis(triphenyltin) sulfide, bis (trimethylsilyl) sulfide or phosphorus pentasulfide. The reaction is expediently carried out in an organic solvent or a solvent mixture, at room temperature or higher, preferably at the boiling temperature of the reaction mixture and if possible under anhydrous conditions. Carbon disulfide, toluene, xylene, pyridine or 1,2-dichloroethane, for example, are suitable. When using the tin or silyl sulfides mentioned, it is appropriate to carry out the sulfurizing reaction in the presence of a Lewis acid such as boron trichloride.

In the presence of other carbonyl groups, these can optionally be protected by a suitable protective group, e.g. by acetalization, according to known methods, before the sulfurizing reaction.

The abovementioned method C preferably proceeds under the following conditions:

The reaction is carried out by reaction of a compound of the formula I, where I is as defined under C), with one or more molar equivalents of a compound of the formula IV, preferably 1.5 to 4 molar equivalents. If appropriate, salts of the compounds of the formula IV, preferably salts of hydrohalic acids, in particular hydrochloric acid, can also be used.

The reaction can be carried out without further components or with addition of acid or base. In particular, when using a salt of a compound of the formula IV, an equivalent of a base can be used to liberate the free amine or hydroxylamine.

The reaction is expediently carried out in an organic solvent. Aromatic hydrocarbons such as toluene or xylene, lower alcohols such as methanol, ethanol, methyl glycol or 1-butanol, ethers such as tetrahydrofuran or glycol dimethyl ether, basic solvents such as pyridine or N-methylimidazole or mixtures of these solvents, for example, are suitable.

The reaction temperature can be between 0 and 200° C., preferably between 20° C. and the boiling point of the solvent or solvent mixture used.

The abovementioned method D preferably proceeds under the following conditions:

The reaction is carried out by reaction of a compound of the formula II with a stochiometric amount or an excess of a reductant. Reductants which can be used are, in particular, complex metal hydrides such as, for example, $NABH_4$, $LiBH_4$ or $LiAlH_4$.

The reaction is expediently carried out in an inert organic solvent. Depending on the reductants used, aromatic hydrocarbons such as toluene or xylene, lower alcohols such as methanol or ethanol, ethers such as tetrahydrofuran or glycol dimethyl ether, or mixtures of these solvents, for example, are suitable.

The reaction temperature can be between 0° C. and 200° C., preferably between 0° C. and the boiling point of the solvent used.

The abovementioned method E preferably proceeds under the following conditions:

The reaction is expediently carried out in a solvent. Aromatic hydrocarbons such as toluene or xylene, water, lower alcohols such as methanol, ethanol, methyl glycol or 1-butanol, ethers such as tetrahydrofuran or glycol dimethyl ether, for example, are suitable.

The reaction temperature can be between 0 and 200° C., preferably between 20° C. and the boiling point of the solvent or solvent mixture used.

The abovementioned method F preferably proceeds under the following conditions:

The substituent B in the formula V is a suitable leaving group, such as, for example, chlorine, bromine or iodine, a suitable radical of sulfuric acid, an aliphatic or aromatic sulfonic acid ester or optionally halogenated acyloxy.

The reaction is expediently carried out in a solvent in the presence of a suitable base to trap the acid liberated in the reaction.

Solvents which can be used are aromatic hydrocarbons such as toluene or xylene, lower alcohols such as methanol, ethanol, methyl glycol or 1-butanol, ethers such as tetrahydrofuran or glycol dimethyl ether, dipolar aprotic solvents such as N,N-dimethylformamide, N-methylpyrrolidone, acetonitrile, nitrobenzene, dimethyl sulfoxide or mixtures of these solvents.

Suitable bases are, for example, alkali metal or alkaline earth metal carbonates or hydrogencarbonates such as sodium hydrogencarbonate, sodium carbonate or calcium carbonate, alkali metal or alkaline earth metal hydroxides such as potassium hydroxide or barium hydroxide, alkoxides such as sodium ethoxide or potassium tert-butoxide, organolithium compounds such as butyllithium or lithium diisopropylamide, alkali metal or alkaline earth metal hydrides such as sodium hydride or calcium hydride, alkali metal fluorides such as potassium fluoride or an organic base such as triethylamine or pyridine.

Two-phase systems with aqueous solutions of bases in the presence of a phase-transfer catalyst such as, for example, benzyltriethylammonium chloride, are also possible.

In some cases the addition of an iodine salt, e.g. lithium iodide, is appropriate.

The reaction is usually carried out at temperatures between −10 and 160° C., preferably at room temperature or the boiling temperature of the solvent.

The pharmaceuticals according to the invention can be administered enterally (orally), parenterally (intravenously), rectally, subcutaneously, intramuscularly or locally (topically).

They can be administered in the form of solutions, powders (tablets, capsules including microcapsules), ointments (creams or gels) or suppositories. Possible auxiliaries for formulations of this type are the pharmaceutically customary liquid or solid fillers and extenders, solvents, emulsifiers, lubricants, flavor corrigents, colorants and/or buffer substances.

As an expedient dose, 0.1–10, preferably 0.2–8 mg/kg of body weight are administered one or more times daily. The dose units used depend expediently on the respective pharmacokinetics of the substance used or of the pharmaceutical preparation used.

The dose unit of the compounds used according to the invention is, for example, 1–1500 mg, preferably 50–500 mg.

The compounds according to the invention can also be administered in combination with other antiviral agents, such as, for example, nucleoside analogs, protease inhibitors or adsorption inhibitors and immunostimulants, interferons, interleukins and colony-stimulating factors (e.g. GM-CSF, G-CSF, M-CSF).

Activity Tests

Testing of Preparations Against HIV Cell Culture

Description of Method

Medium:
RPMI pH 6.8

Complete medium additionally contains 20% fetal calf serum and 40 IU/ml of recombinant interleukin 2.

Cells:
Lymphocytes isolated from fresh donor blood by means of Ficoll$^R$ gradient centrifugation are cultured at 37° C. under 5% $CO_2$ for 36 h in complete medium with addition of 2 g/ml of phytohemagglutinin (Wellcome). After addition of 10% DMSO, the cells are frozen at a cell density of $5 \times 10^6$ and stored in liquid nitrogen. For the experiment, the cells are thawed, washed in RPMI medium and cultured in complete medium for 3–4 days.

Batch:
The test preparations were dissolved in DMSO in a concentration of 16.7 mg/ml and diluted to 1 mg/ml in complete medium. 0.4 ml of medium was initially introduced into 24-well multiwell dishes. After addition of 0.1 ml of the dissolved preparation in the top row of the dish, a geometrical dilution series was produced by transfer of 0.1 ml in each case. Preparation-free controls always contained 0.4 ml of complete medium containing 0.5% DMSO. Lymphocyte cultures having a cell count of $5 \times 10^5$ cells/ml were infected by addition of 1/50 volumes of supernatant from HIV-infected lymphocyte cultures. The titer of these culture supernatants was determined by endpoint dilution with $1–5 \times 10^6$ infectious units/ml. After incubation at 37° C. for 30 min, the infected lymphocytes were removed by centrifugation and taken up again in the same volume of medium. 0.6 ml of this cell suspension in each case was added to all hollows of the test plate. The batches were incubated at 37° C. for 3 days.

Evaluation:
The infected cell cultures were investigated under the microscope for the presence of giant cells, which indicate active virus replication in the culture. The lowest preparation concentration at which no giant cells occurred was determined as the inhibitory concentration against HIV. For the control, the supematants from the culture plates were determined for the presence of HIV antigen using an HIV antigen test according to the instructions of the manufacturer (Organon).

Results:
Table 1 shows the results of this test.

TABLE 1

| Compound number | MIC (ng/ml) | EC-50 (ng/ml) |
|---|---|---|
| 5 | 200 | 5 |
| 15 | >40 | ≈20 |
| 16 | >40 | 50 |
| 18 | >200 | ≈80 |
| 19 | ≈200 | ≈20 |
| 20 | >8 | ≈2 |
| 30 | ≈200 | ≈40 |
| 34 | >200 | ≈100 |
| 35 | >40 | >8 |
| 39 | >200 | 30 |
| 40 | >40 | 15 |

TABLE 1-continued

| Compound number | MIC (ng/ml) | EC-50 (ng/ml) |
|---|---|---|
| 41 | >40 | <1 |
| 42 | >200 | ≈100 |
| 45 | <200 | ≈40 |
| 61 | ≈80 | n.d. |
| 70 | ≈400 | <80 |
| 71 | ≈400 | <80 |
| 101 | ≈2000 | ≈400 |

Investigation of the Substances for Inhibition of HIV "Reverse Transcriptase"

The activity of the reverse transcriptase (RT) was determined using a "Scintillation Proximity Assay" (SPA).

The reagent kit for the RT-SPA was obtained from Amersham/Buchler (Brunswick). The enzyme RT (from HIV cloned in *E. coli*) came from HT Biotechnology LTD, Cambridge, UK.

Batch:
The test was carried out according to the method manual of the manufacturer Amersham—with the following modifications:

Bovine serum albumin was added to the assay buffer to a final concentration of 0.5 mg/ml.

The test was carried out in Eppendorf reaction vessels with a 100 ml batch volume.

The RT concentrate of the manufacturer (5000 U/ml) was diluted to an activity of 15 U/ml in tris HCl buffer 20 mM; pH 7.2; 30% glycerol.

The incubation time for the batches was 60 min (37° C.).

After stopping the reaction and "development" with the bead suspension, 130 µl batches were transferred to 4.5 ml of tris HCl buffer, 10 mM; pH 7.4; 0.15 M NaCl and the tritium activity was measured in a β-counter.

Substance testing:
For a preliminary test of the inhibitor activity, the substances were dissolved in DMSO (stock solution c=1 mg/ml) and tested in dilution in DMSO $10^{-1}$, $10^{-2}$, $10^{-3}$ etc.

For the determination of $IC_{50}$ values, the inhibitor stock solutions were further diluted in tris HCl buffer, 50 mM, pH 8 and tested in suitable concentrations.

From the graphic representation of RT activity versus Log $C_{Inh}$, the concentration associated with a 50% enzyme inhibition was determined.

Table 2 shows the results of the investigation.

TABLE 2

| Compound number | Reverse Transcriptase Assay IC-50 |
|---|---|
| 5 | 0.035 µM/ml |
| 6 | 0.022 µM/ml |
| 15 | 0.021 µM/ml |
| 16 | 0.372 µM/ml |
| 18 | 0.029 µM/ml |
| 19 | 0.094 µM/ml |
| 20 | 0.008 µM/ml |
| 30 | 0.147 µM/ml |
| 34 | 0.415 µg/ml |
| 35 | 0.153 µg/ml |
| 40 | 0.170 µg/ml |
| 31 | 0.007 µM/ml |
| 43 | 0.026 µM/ml |
| 45 | 0.034 µM/ml |
| 61 | 0.026 µM/ml |
| 67 | 0.001 µM/ml |
| 70 | 0.008 µM/ml |

TABLE 2-continued

| Compound number | Reverse Transcriptase Assay IC-50 |
|---|---|
| 71 | 0.001 μM/ml |
| 101 | 0.041 μg/ml |

The present invention is explained in greater detail by means of the following examples and by means of the contents of the patent claims.

PREPARATION OF THE STARTING MATERIALS

EXAMPLE I

Synthesis of 5-chloro-1-propionylisatin 18.2 g (0.1 mol) of 5-chloroisatin (Lancaster) are suspended in 10 ml of propionic anhydride and heated under reflux for 2.5 hours with stirring. For working-up, the excess propionic anhydride is distilled off from the reaction mixture under reduced pressure and the residue which remains is treated with 200 ml of diethyl ether after cooling to room temperature. The precipitated solid is filtered off and dried in vacuo.

14.9 g of 5-chloro-1-propionylisatin are obtained; red crystals of melting point 160–162° C. (yield: 63% of theory).

EXAMPLE II

Synthesis of 5-chloro-3-(1-carboxyprop-1-ylene) indolin-2-one 5 g (30 mmol) of 5-chloroindolin-2-one, dissolved in 40 ml of abs. ethanol, are added at room temperature to a solution of 2.1 g (90 mmol) of sodium in 70 ml of absolute ethanol. After addition is complete, the reaction mixture is treated with 3.06 g (30 mmol) of 2-oxobutyric acid in 40 ml of abs. ethanol and heated under reflux for 3 hours. The reaction product crystallizes out on cooling and is filtered off from the reaction solution, then suspended in 50 ml of water, acidified with 2N aqueous HCl and separated off from the solution.

3.6 g of yellow crystals of melting point 224–226° C. are obtained, yield 48% of theory.

EXAMPLE III

Preparation of 5-methoxyisatin

Stage 1: Synthesis of p-methoxyisonitrosoacetanilide 90 g of chloral hydrate are suspended in 1200 ml of water and treated with 1300 g of sodium sulfate decahydrate with stirring. This reaction mixture is treated successively with 61.5 g of p-methoxyaniline (0.5 mol), 300 ml of water, 44 ml (0.52 mol) of conc. hydrochloric acid and with 110 g (1.58 mol) of hydroxylamine hydrochloride, dissolved in 500 ml of water. The reaction solution is heated under reflux for 5 min. It is then allowed to cool to room temperature, in the course of which the reaction product crystallizes out. The precipitated acetanilide is filtered off, washed with a little water and dried in vacuo.

84.2 g of pale brown crystals of melting point 182° C. are obtained, yield 87% of theory.

$^1$H-NMR (200 MHz, $d_6$-DMSO): δ =3.75 (s, 3H), 6.89 (m, 2 H), 7.60 (m, 2 H), 7.68 (s, 1 H), 10.1 (br s, 1H), 12.05 (s, 1H); MS: $(M+H)^+$=195

Stage 2: Synthesis of the Final Product 69 g of the compound prepared in Stage 1 are dissolved in 550 ml of 90% aqueous sulfuric acid, the temperature of the solution rising from room temperature to 55° C. It is then stirred at this temperature for 30 minutes and the solution is then added to 5 l of ice water. The precipitated reaction product is filtered off, washed and dried in an oil-pump vacuum.

40 g of colorless crystals of melting point 190° C. are obtained, yield 64% of theory.

$^1$H-NMR (200 MHz, $d_6$-DMSO): δ=3.76 (s, 3 H), 6.85 (d, J=8.5 Hz, 1H), 7.06 (d, J=2 Hz, 1 H), 7.20 (dd, 1 H), 10.82 (s, 1 N-H); MS: $(M+H)^+$=178.

PREPARATION OF THE FINAL PRODUCTS

EXAMPLE 1

Preparation of 6-chloro-3-methylquinolin-2(1H)-one-4-carboxylic acid (VI.13 in Table 4)

10.9 g (45.9 mmol) of the compound prepared in Example 1 are suspended in 150 ml of water and treated with 2.1 equivalents of NaOH (3.9 g) with stirring. The reaction mixture is then heated under reflux for 1 hour. For working-up, the still hot solution is treated with 1 g of active carbon and filtered through Celite (Aldrich). The filtrate obtained in this way is acidified by means of conc. hydrochloric acid with ice-cooling. After removal of the solvent under reduced pressure, the reaction product is obtained as a salmon-colored solid.

The following is obtained: 8.1 g of 6-chloro-3-methylquinolin-2(1H)-one-4-carboxylic acid of melting point >300° C.; yield: 74% of theory.

$^1$H-NMR (200 MHz, $d_6$-DMSO): δ=2.09 (s, 3 H), 7.3–7.7 (3 m, 3 H), 11.15 (brs, 1 N-H), 12.15 (brs, 1 N-H), 13.4–14.6 (brs, 1 COOH); MS: $(M+H)^+$=238.

EXAMPLE 2

Preparation of 6-chloro-3-methylquinolin-2(1H)-one-4-carbonyl chloride 6.5 g (0.027 mol) of the carboxylic acid prepared in Example 1 are dissolved in 80 ml of thionyl chloride and heated under reflux for two hours. For working-up, the reaction mixture is concentrated under reduced pressure on a rotary evaporator and the residue which remains is stirred with diethyl ether. The reaction product is filtered off and the solid obtained is dried in vacuo.

5.6 g of reddish-colored crystals of melting point 179° C. (81% of theory) are obtained.

The reaction product obtained in this way is used for further reactions without further purification (see Example 3).

EXAMPLE 3

Preparation of 6-chloro-4-hydroxymethyl-3-methylquinolin-2(1H)-one 1.28 g (5 mmol) of the acid chloride prepared in Example 2 are dissolved in 50 ml of absolute tetrahydrofuran (THF) and treated with 0.38 g (10 mmol) of sodium borohydride and 0.5 ml of water with stirring. The mixture is then heated under reflux for 1 hour.

For working-up, the reaction solution is concentrated under reduced pressure on a rotary evaporator, the residue is taken up in 100 ml of water and the mixture is acidified with 20% aqueous citric acid solution. The precipitated solid is filtered off and dried in vacuo.

0.720 g of colorless crystals of melting point 330° C. (product melts with decomposition) is obtained: yield 64%.

$^1$H-NMR (200 MHz, d$_6$-DMSO): δ=2.18 (s; 3 H), 4.71 (d, J=9 Hz, 2), 5.32 (t, J=9 Hz, 1 OH), 7.28 (d, J=8 Hz), 7.50 (dd, J=2 Hz), 7.89 (d, 1 H), 1 1.85 (br s, 1 N-H); MS: (M+H)$^+$=224.

EXAMPLE 4

Preparation of 4-acetoxymethyl-6-chloro-3-methylquinolin-2(1H)-one and 4-acetoxymethyl-1-acetyl-6-chloro-3-methylquinolin-2(1H)-one 700 mg (3.13 mmol) of the hydroxymethyl compound prepared according to Example 3 are dissolved in 50 ml of acetic anhydride and treated with 3 g of sodium acetate. The reaction mixture is heated at 100° C. for 2 hours. For working-up, it is concentrated under reduced pressure on a rotary evaporator and the residue which remains is extracted with methylene chloride/water. The organic phase is dried by means of sodium sulfate and the solvent is removed under reduced pressure on a rotary evaporator. The crude product obtained in this way consists of 2 reaction products, which are isolated by means of chromatography on silica gel (mobile phase: n-heptane/ethyl acetate=2/1).

After chromatographic purification and removal on a rotary evaporator of the eluent used, both reaction products are obtained in crystalline form after stirring the respective fractions with diethyl ether. The two compounds are 4-acetoxymethyl-6-chloro-3-methylquinolin-2(1H)-one and 4-acetoxymethyl-1-acetyl-6-chloro-3-methylquinolin-2(1H)-one.

4-Acetoxymethyl-6-chloro-3-methylquinolin-2(1H)-one Yield: 480 mg, colorless crystals of melting point 220° C.; R$_F$ (n-heptane/ethyl acetate=2:1)=0.08.

$^1$H-NMR (200 MHz, d$_6$-DMSO):=2.06 (s, 3 H), 2.21 (s, 3 H), 5.39 (ps s, 2 H), 7.32 (s, J=8 Hz, 1 H), 7.51 (dd, J=2 Hz, 1H), 7.81 (d, 1 H); MS: (M+H)$^+$=266.

4-Acetoxymethyl-1-acetyl-6-chloro-3-methylquinolin-2 (1H)-one Yield: 270 mg, colorless crystals of melting point 116° C.; R$_F$ (n-heptane/ethyl acetate=2:1)=0.23.

$^1$H-NMR (200 MHz, d$_6$-DMSO): δ=2.04 (s, 3 H), 2.38 (s, 3H), 2.42 (s, 3 H), 5.59 (m, 2H), 7.79 (dd, J=9 and 2 Hz, 1 H), 7.95 (d, 1 H), 8.26 (d, 1H); MS: (M+H)$^+$=308.

EXAMPLE 5

Synthesis of 4-acetoxymethyl-6-chloro-3-methylquinoline-2(1H)-thione 266 mg (1 mmol) of 4-acetoxymethyl-6-chloro-3-methylquinolin-2(1H)-one (see Example 4) are suspended in 40 ml of absolute toluene and treated with 222 mg (0.55 mmol) of Lawesson's reagent (2,4-bis-(4-methoxyphenyl)-1,3-dithia-2,4-diphosphetane-2,4-disulfide) and heated at 100° C. for 1 hour. For working-up, the reaction mixture is concentrated under reduced pressure on a rotary evaporator and the crude product is purified by means of chromatography on silica gel (mobile phase: n-heptane/ethyl acetate= 4/1). A yellow oil is obtained, which is afforded in crystalline form after addition of n-pentane.

Yield: 90 mg, yellow crystals of melting point 235° C., R$_F$ (n-heptane/ethyl acetate=2:1)=0.46.

$^1$H-NMR (200 MHz, d$_6$-DMSO): δ=2.03 (s, 3H), 3.29 (s, 3 H), 5.45 (ps s, 2 H), 7.60–7.75 (m, 2 H), 7.97 (ps s, 1 H), 13.95 (br s, 1 N-H); MS: (M+H)$^+$=282.

EXAMPLE 6

Preparation of 3-phenylquinolin-2(1H)-one-4-carboxylic acid (VI.1 in Table 4)

25 g of isatin (0.17 mol) are heated at 220° C. with 50.9 g (0.374 mol) of phenylacetic acid and 2.5 g of anhydrous sodium acetate for 30 min with stirring. After addition of 150 ml of glacial acetic acid at this temperature, the reaction mixture is allowed to cool and is treated with ice water. The precipitated reaction product is filtered off and dried in vacuo. The crude product is recrystallized from glacial acetic acid using active carbon.

The following is obtained: 21.3 g of phenylquinolin-2 (1H)-one-4-carboxylic acid of melting point 288° C. in the form of pale beige crystals; yield: 74% of theory.

$^1$H-NMR (200 MHz, d$_6$-DMSO): δ=7.20–7.65 (m, 9 H), 12.16 (br s, 1 N-H, 13.8–14.0 (br s, 1-COOH); MS: (M+H)$^+$=266.

EXAMPLE 7

Preparation of isopropyl 3-phenylquinolin-2(1H)-one-4-carboxylate 1.42 g (5 mmol) of the acid chloride prepared from compound 6 by means of the process described in Example 2 are dissolved in 25 ml of absolute isopropanol which has previously been treated with 0.290 g (12.5 mmol) of sodium metal. The reaction mixture is then heated at reflux temperature for 4 hours. After completion of the reaction, the reaction mixture is concentrated on a rotary evaporator under reduced pressure, the residue which remains is stirred with water and the precipitated solid is filtered off with suction. For further purification of the reaction product, it is recrystallized from isopropanol using active carbon.

0.8 g of slightly pink-colored crystals of melting point 211–212° C. are obtained; (RF value=0.57 (mobile phase: ethyl acetate/n-heptane=2/1); yield 52% of theory.

$^1$H-NMR (200 MHz, d$_6$-DMSO): δ=0.98 (d, J=7 Hz, 6 H), 4.97 (hept, 1 H), 7.20–7.65 (m, 9 H), 12.22 (br s, 1 N-H); MS: (M+H)$^+$=308

EXAMPLE 8

Preparation of isopropyl 3-phenylquinoline-2(1H)-thione-4-carboxylate 307 mg (1 mmol) of isopropyl 3-phenylquinolin-2(1H)-one-4-carboxylate (Example 7) are reacted with Lawesson's reagent according to the process described in Example 5 and purified by chromatography on silica gel as indicated above (mobile phase: n-heptane/ethyl acetate=411).

0.29 g of yellowish crystals of melting point 235° C. is obtained; yield 90% of theory.

$^1$H-NMR (200 MHz, d$_6$-DMSO): δ=0.95 (d, J=7 Hz, 6 H), 4.91 (hept, 1 H), 7.18–7.24 (m, 2H), 7.35–7.55 (m, 5 H), 7.64–7.80 (m, 2 H), 14.02 (br s, 1 N-H); MS: (M+H)$^+$=324.

EXAMPLE 9

Preparation of 6-chloro-3-ethylquinolin-2(1H)-one-4-carboxylic acid (VI.14 in Table 4)

3.4 g of 5-chloro-3-(1-carboxylprop-1-ylene) indolin-2-one (Example II) are suspended in 270 ml of 2 n HCl and heated under reflux for 20 hours. After completion of the reaction, it is allowed to cool to room temperature and the crystallized reaction product is filtered off. For further purification of the carboxylic acid obtained, this is stirred again with a mixture of 100 ml of water and 100 ml of ethanol, filtered off and dried.

1.45 g of brown crystals of melting point 215–217° C. are obtained, yield: 42% of theory.

$^1$H-NMR (200 MHz, d$_6$-DMSO): δ=1.13 (t, J=7.5 Hz, 2 H), 2.52 (q, 2H), 7.15–7.6 (m, 3 H), 12.15 (br s, 1H, N-H), 13.0–14.6 (br s, 1 COOH); MS: (M+H)$^+$=252.

EXAMPLE 10

Preparation of isopropyl 6-chloro-3-ethylquinolin-2(1H)-one-4-carboxylate 1.45 g (6 mmol) of the acid chloride prepared from the compound of Example 9 by means of the process described in Example 2 are dissolved in 25 ml of absolute isopropanol which has previously been treated with 0.173 g (7.5 mmol) of sodium metal and the reaction mixture is then heated under reflux for 3 hours. After completion of the reaction, the suspension obtained is concentrated on a rotary evaporator under reduced pressure, the residue which remains is taken up using 200 ml of ethyl acetate and the organic phase is washed with water. The crude product is then dried by means of sodium sulfate and the organic solvent is removed on a rotary evaporator under reduced pressure. The resultant yellow oil is purified by means of chromatography on silica gel (mobile phase: n-heptane/ethyl acetate=1/1).

Yield: 0.280 g (32% of theory, colorless crystals of melting point 179–180° C.

$^1$H-NMR (200 MHz, d6-DMSO): δ=1.09 (t, J=7.5 Hz, 3 H), 1.38 (d, J=7 Hz, 6 H), 2.49 (q, 2 H), 5.37 (hept, 1 H), 7.34 (d, J=2 Hz), 7.36 (d, J=8 Hz), 7.58 (dd, 1H), 12.18 (br s, 1 H); MS: (M+H)$^+$=294.

EXAMPLE 11

Preparation of isopropyl 6-chloro-3-ethylquinoline-2(1H)-thione-4-carboxylate 150 mg (0.51 mmol) of isopropyl 6-chloro-3-ethylquinolin-2(1H)-one-4-carboxylate (Example 10) are reacted with Lawesson's reagent according to the process described in Example 5 (reaction time 5 hours at reflux temperature) and purified by means of chromatography on silica gel as indicated above (mobile phase: n-heptane/ethyl acetate=2/1).

0.13 g of yellowish crystals of melting point 194–196° C. is obtained; yield: 90% of theory.

$^1$H-NMR (200 MHz, d$_6$-DMSO): δ=1.18 (t, J=7.5 Hz, 3 H), 1.40 (d, J=7 Hz, 6 H), 3.86 (q, 2 H), 5.39 (hept, 1 H), 7.45 (ps s, 1 H), 7.65–7.80 (m, 2 H), 14.05 (bs s, 1 N-H); MS: (M+H)$^+$=310.

EXAMPLE 12

Preparation of 6-methoxy-3-phenylquinolin-2(1H)-one-4-carboxylic acid (VI.21 in Table 4)

8.5 g of 5-methoxyisatin (50 mmol, Example III) are reacted with 15 g (50 mmol) of phenylacetic acid according to the process described in Example 6. For working-up, the mixture is treated with 600 ml of ice water and the solution is extracted twice with 100 ml of dichloromethane in each case after alkalization by means of conc. NaOH. The aqueous phase is then acidified by using conc. hydrochloric acid and the precipitated reaction product is filtered off.

10.9 g of gray-colored crystals are obtained, which melt with decomposition at 320° C.; yield: 74% of theory.

$^1$H-NMR (200 MHz, d$_6$-DMSO): δ=3.79 (s, 3 H), 6.88 (m, 1 H), 7.20–7.48 (m, 7 H), 12.05 (br s, 1H), 13.8 (br s, 1 H); MS: (M+H)$^+$=296.

EXAMPLE 13

Preparation of isopropyl 6-methoxy-3-phenylquinolin-2(1H)-one-4-carboxylate 3.1 g (10 mmol) of the acid chloride prepared from the compound of Example 12 by means of the process described in Example 2 are dissolved in 50 ml of absolute isopropanol which has previously been treated with 0.58 g (25 mmol) of sodium metal, and the reaction mixture is heated for 4 hours at 50° C. and then stirred for 4 hours at room temperature. After completion of the reaction, the suspension obtained is concentrated under reduced pressure on a rotary evaporator, the residue which remains is stirred with 100 ml of 20% aqueous citric acid solution and the reaction product is filtered off with suction. For further purification of the crude product, it is recrystallized from absolute ethanol using active carbon.

2 g of reddish colored crystals of melting point 231° C. are obtained; yield 60% of theory.

$^1$H-NMR (200 MHz, d$_6$-DMSO): δ=1.02 (d,J=7 Hz, 6 H), 3.78 (s, 3 H), 4.99 (hept, 1 H), 6.83 (d, J=2 Hz, 1 H), 7.22–7.48 (m, 7 H), 12.15 (br s, 1 N-H); MS: (M+H)$^+$=338.

EXAMPLE 14

Preparation of isopropyl 6-methoxy-3-phenylquinoline-2(1H)-thione-4-carboxylate 1 g (3 mmol) of 6-methoxy-3-phenylquinolin-2(1H)-one-4-carboxylate (Example 13) is reacted with 1.1 equivalents of Lawesson's reagent according to Example 5 (reaction time 1 hour; reaction temperature: 100° C.). After concentration of the solution, the reaction product is purified by means of chromatography on silica gel (mobile phase: n-heptane/ethyl acetate=1/1).

840 mg of yellow crystals of melting point 219° C. are obtained, yield 79% of theory.

$^1$H-NMR (200 MHz, d$_6$-DMSO): δ=0.96 (d, J=7 Hz, 6 H), 3.80 (s, 3 H), 4.93 (hept, 1 H), 6.82 (d, J=2 Hz, 1 H), 7.16–7.24 (m, 2 H), 7.32–7.45 (m, 4 H), 7.72 (d, J=9 Hz, 1 H), 14.02 (br s, 1 N-H); MS: (M+H)$^+$=354.

EXAMPLE 15

Preparation of 6-chloro-3-(p-chlorophenyl)-4-isopropoxycarbonylquinolin-2(1H)-one-2-O-methyl oxime 0.42 g (1.07 mol) of 6-chloro-3-(p-chlorophenyl)-4-isopropoxycarbonylquinoline-2(1H)-thione (prepared according to methods from Examples 6, 7 and 8 described above, but using 5-chloroisatin and p-chlorophenyl acetic acid as starting materials) is dissolved in 10 ml of abs. ethanol and treated with 0.5 g of O-methylhydroxylamine hydrochloride. The reaction mixture is heated at reflux temperature for 3 hours. It is then concentrated under reduced pressure on a rotary evaporator, the residue is taken up in ethyl acetate, the organic phase is washed twice with water and, after drying by means of sodium sulfate, concentrated under reduced pressure on a rotary evaporator. The crude product obtained is purified by means of chromatography on silica gel (mobile phase: ethyl acetate/n-heptane= 1/4). For fine purification, chromatography on ®Sephadex type LH-20 using methanol as the mobile phase is suitable.

80 mg of yellow crystals of melting point 178–180° C. are obtained, yield 18% of theory.

$^1$H-NMR (200 MHz, d$_6$-DMSO): δ 0.93 (d, J=7 Hz, 6H), 3.68 (s, 3 H), 4.90 (hept, 1 H), 7.11 (d, J=2 Hz, 1 H), 7.22–7.34 (m, 2 H), 7.40–7.56 (m, 4 H), 10.40 (br s, 1 N-H); MS: (M+H)$^+$=405.

EXAMPLE 16

Preparation of 4-benzoyl-6-chloro-3-phenylquinoline -2(1H)-one 1 g (3.1 mmol) of 6-chloro-3-phenylquinolin-2(1H)-one-4-carbonyl chloride (prepared in analogy to the processes described in Examples 6 and 2, but using 5-chloroisatin and phenylacetic acid as starting components) is dissolved in 30 ml of abs. tetrahydrofuran and cooled to −50° C. 2.1 ml (2 molar equivalents) of a 3 molar ethereal solution are then added dropwise. After addition is complete, the mixture is stirred for 30 min at 40° C. and 2 hours at 20° C.

For working-up, the reaction mixture is poured onto 20% strength aqueous citric acid solution and this solution is extracted twice with 150 ml of ethyl acetate. The combined organic phases are dried over Na$_2$SO$_4$ and concentrated on a rotary evaporator under reduced pressure. The crude product is obtained as a pale yellow oil which is purified by means of chromatography on silica gel (mobile phase ethyl acetate/n-heptane=3/2).

140 mg of slightly pink-colored crystals of melting point 266–267° C. are obtained [R$_F$(ethyl acetate/n-heptane=1/1): δ=0.24], yield 13% of theory.

$^1$H-NMR (200 MHz, d$_6$-DMSO): δ=7.05–7.78 (m, 13H), 12.42 (br s, 1H); MS: (M+H)=360.

Table 3 which follows gives an overview of the synthesized compounds. All derivatives were characterized by means of $^1$H-NMR spectrum, mass spectrum and by means of the respective melting point.

TABLE 3

Synthesized derivatives of the formulae (1) and (1a)

The derivatives of the formulae I and Ia shown in Table 3 were prepared, inter alia, from the appropriate carboxylic acids of the formulae VI or VIa, which can be synthesized by the methods described in Examples 1, 6, 9 and 12. The compounds of the formulae VI and VIa are either known from the literature or can be prepared in analogy to processes known from the literature (cf., for example: J. Am. Chem. Soc. 1953, 75, 5305; Ind. J. Chem. 1987, 26B, 910; Synthesis 1985, 541; J. Heterocyclic Chem. 1979, 16, 487; J. Heterocyclic Chem. 1989, 26, 281; Ber. 1894, 26, 2484; Bull. Chem. Soc. Japan 1977, 50(8), 1959; J. Org. Chem. 1972, 37, 3967; Chem. Pharm. Bull. 1992, 40, 1322; in addition textbooks of organic chemistry e.g. "The Chemistry of Heterocyclic Compounds", E. C. Taylor (Ed.), Wiley & Sons, New York or "Advances in Heterocyclic Chemistry", A. R. Katritzky (Ed.), Academic Press, San Diego). Furthermore; the isatin or indolin-2-one derivatives used as starting materials are either commercially available or can be synthesized by known processes described in the literature (cf., for example, J. Org. Chem. 1977, 42, 1344; J. Prakt. Chem. 1940, 155, 234; Org. Syntheses, Coll. Vol. 1, 327 (1941); Ind. J. Chem 1990, 29B, 578; Pharmazie 1984, 39, 153; Ind. J. Chem 1987, 26B, 535; J. Am. Chem. Soc. 1974, 96, 5512; J. Org. Chem. 1979, 44, 628; J. Med. Chem. 1992, 35, 2085; in addition textbooks of organic chemistry, e.g. "The Chemistry of Heterocyclic Compounds", E. C. Taylor (Ed.), Wiley & Sons, New York or "Advances in Heterocyclic Chemistry", A. R. Katritzky (Ed.), Academic Press, San Diego).

| Compound number | Structure | Melting point (in ° C.) | Preparation according to Ex.: Yield in % | Starting material employed |
|---|---|---|---|---|
| 1 | 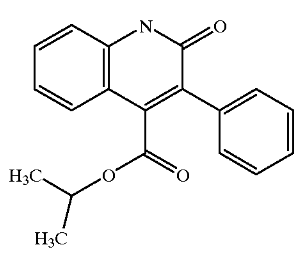 | 212 | see Example 7.52% | VI.1 |
| 2 | 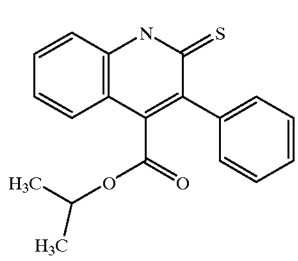 | 235 | see Example 8.90% | 1 |

TABLE 3-continued

Synthesized derivatives of the formulae (1) and (1a)

| # | Structure | mp (°C) | Method | Ref. |
|---|---|---|---|---|
| 3 | 6-chloro-2-oxo-3-phenyl-quinoline-4-carboxylic acid isopropyl ester | 246 | analogously to example 7.63 | VI.2 |
| 4 | 3-ethyl-2-oxo-quinoline-4-carboxylic acid isopropyl ester | 124–126 | analogously to example 7.58% | VI.3 |
| 5 | 3-ethyl-2-thioxo-quinoline-4-carboxylic acid isopropyl ester | 154–155 | analogously to example 5.82% | 4 |
| 6 | 6-chloro-3-phenyl-2-thioxo-quinoline-4-carboxylic acid isopropyl ester | 234 | analogously to example 5.78% | 3 |
| 7 | 2-oxo-3-phenyl-quinoline-4-carboxylic acid methyl ester | 248–252 | analogously to example 7.84% | VI.1 |
| 8 | 6-chloro-2-oxo-3-phenyl-quinoline-4-carboxylic acid (1-ethyl-propyl) ester | 190–193 | analogously to example 7.27% | VI.2 |

TABLE 3-continued
Synthesized derivatives of the formulae (1) and (1a)
| | | | | |
|---|---|---|---|---|
| 9 | 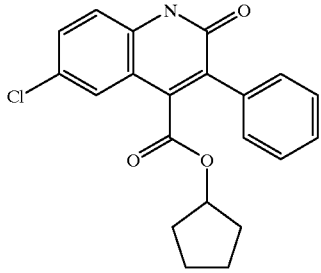 | 211–214 | analogously to example 7.68% | VI.2 |
| 10 | 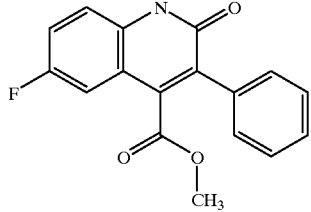 | 287–289 | analogously to example 7.96% | VI.5 |
| 11 | 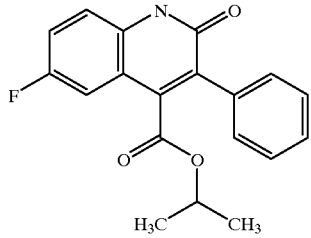 | 233–236 | analogously to example 7.90% | VI.5 |
| 12 | 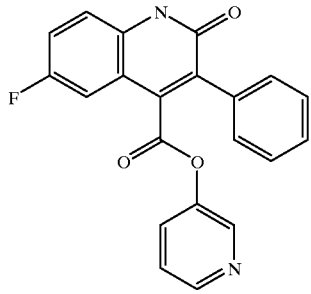 | 254–257 | analogously to example 7.78% | VI.5 |
| 13 | 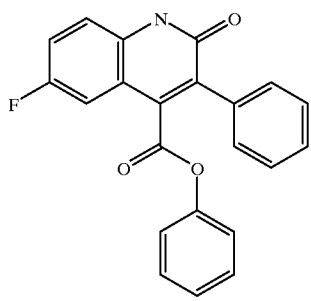 | 263–265 | analogously to example 7.71% | VI.5 |

TABLE 3-continued

Synthesized derivatives of the formulae (1) and (1a)

| # | Structure | mp (°C) | Method | Yield | Ref |
|---|---|---|---|---|---|
| 14 | 6-chloro-2-oxo-3-phenyl-quinoline-4-carboxylic acid pyridin-3-yl ester | 253–255 | analogously to example | 7.62% | VI.2 |
| 15 | 6-fluoro-2-thioxo-3-phenyl-quinoline-4-carboxylic acid isopropyl ester | 210–213 | analogously to example | 5.26% | 11 |
| 16 | 2-oxo-3-isobutyl-quinoline-4-carboxylic acid isopropyl ester | 162–164 | analogously to example | 7.35% | VI.4 |
| 17 | 6-chloro-2-oxo-3-phenyl-quinoline-4-carboxylic acid methyl ester | 273–275 | analogously to example | 7.80% | VI.2 |
| 18 | 6-chloro-2-thioxo-3-phenyl-quinoline-4-carboxylic acid pentan-3-yl ester | 185–186 | analogously to example | 5.41% | 8 |

TABLE 3-continued

Synthesized derivatives of the formulae (1) and (1a)

| | | | | |
|---|---|---|---|---|
| 19 | 6-chloro-3-ethyl-2-oxo-1,2-dihydroquinoline-4-carboxylic acid isopropyl ester | 179–180 | see Example 10 | VI.14 |
| 20 | 6-chloro-3-ethyl-2-thioxo-1,2-dihydroquinoline-4-carboxylic acid isopropyl ester | 193–195 | see Example 11 | 19 |
| 21 | 3-methyl-2-oxo-1,2-dihydroquinoline-4-carboxylic acid isopropyl ester | 185 | analogously to example 7.35% | VI.10 |
| 22 | 3-methyl-2-oxo-1,2-dihydroquinoline-4-carboxylic acid cyclopentyl ester | 183 | analogously to example 7.44% | VI.10 |
| 23 | 3-methyl-2-oxo-1,2-dihydroquinoline-4-carboxylic acid methyl ester | 174 | analogously to example 7.68% | VI.10 |
| 24 | 3-methyl-2-oxo-1,2-dihydroquinoline-4-carboxylic acid benzyl ester | 189 | analogously to example 7.59% | VI.10 |

TABLE 3-continued
Synthesized derivatives of the formulae (1) and (1a)
| | | | | |
|---|---|---|---|---|
| 25 | 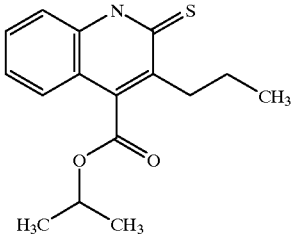 | 179–180 | analogously to example 5.83% | 16 |
| 26 | 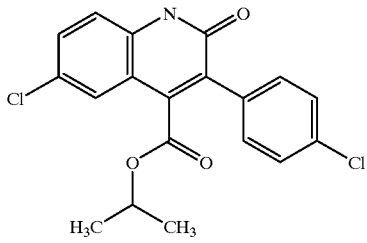 | 210–215 | analogously to example 7.67% | VI.15 |
| 27 | 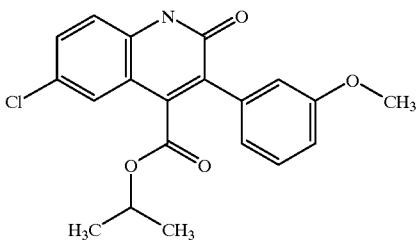 | 268–270 | analogously to example 7.85% | VI.17 |
| 28 | 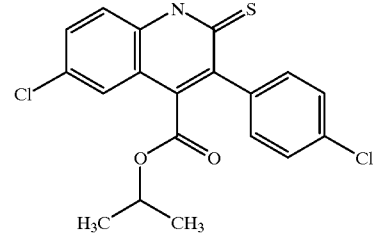 | 220–223 | analogously to example 5.60% | 26 |
| 29 | 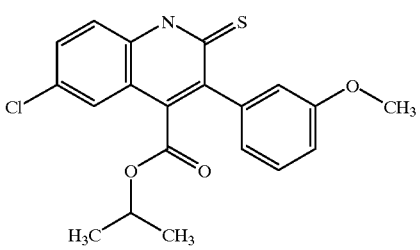 | 216–218 | analogously to example 5.14% | 27 |
| 30 | 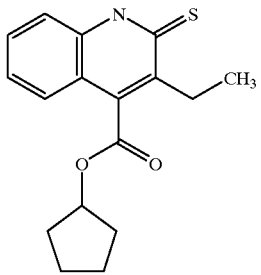 | 169–170 | analogously to example 5.71% | 98 |

TABLE 3-continued

Synthesized derivatives of the formulae (1) and (1a)

| # | Structure | | | |
|---|---|---|---|---|
| 31 | (3-methyl-2-thioxo-1,2-dihydroquinoline-4-carboxylic acid methyl ester) | 217 | analogously to example 5.59% | 23 |
| 32 | (3-methyl-2-thioxo-1,2-dihydroquinoline-4-carboxylic acid isopropyl ester) | 195 | analogously to example 5.86% | 21 |
| 33 | (3-methyl-2-thioxo-1,2-dihydroquinoline-4-carboxylic acid benzyl ester) | 192 | analogously to example 5.74% | 24 |
| 34 | (3-isopropyl-2-oxo-1,2-dihydroquinoline-4-carboxylic acid isopropyl ester) | 140 | analogously to example 7.61% | V.11 |
| 35 | (3-isopropyl-2-thioxo-1,2-dihydroquinoline-4-carboxylic acid isopropyl ester) | 160 | analogously to example 5.95% | 34 |
| 36 | (3-vinyl-2-oxo-1,2-dihydroquinoline-4-carboxylic acid isopropyl ester) | 158 | analogously to example 7.34% | VI.6 |

TABLE 3-continued

Synthesized derivatives of the formulae (1) and (1a)

| # | Structure | | | |
|---|---|---|---|---|
| 37 | (3-methyl-2-thioxo-1,2-dihydroquinoline-4-carboxylic acid cyclopentyl ester) | 191 | analogously to example 5.92% | 23 |
| 38 | (6-chloro-3-methyl-2-oxo-1,2-dihydroquinoline-4-carboxylic acid methyl ester) | 253 | analogously to example 7.62% | VI.13 |
| 39 | (6-chloro-3-methyl-2-thioxo-1,2-dihydroquinoline-4-carboxylic acid methyl ester) | 237 | analogously to example 5.90% | 38 |
| 40 | (6-chloro-3-methyl-2-oxo-1,2-dihydroquinoline-4-carboxylic acid isopropyl ester) | 213 | analogously to example 7.46% | VI.13 |
| 41 | (6-chloro-3-methyl-2-thioxo-1,2-dihydroquinoline-4-carboxylic acid isopropyl ester) | 209 | analogously to example 5.94% | 40 |
| 42 | (6-chloro-3-methyl-2-oxo-1,2-dihydroquinoline-4-carboxylic acid cyclopropylmethyl ester) | 202 | analogously to example 7.59% | VI.13 |

TABLE 3-continued

Synthesized derivatives of the formulae (1) and (1a)

| # | Structure | mp (°C) | Method | Yield | Ref |
|---|---|---|---|---|---|
| 43 | 6-chloro-3-methyl-2-thioxo-1,2-dihydroquinoline-4-carboxylic acid cyclopropylmethyl ester | 187 | analogously to example | 5.90% | 42 |
| 44 | 6-chloro-3-methyl-2-oxo-1,2-dihydroquinoline-4-carboxylic acid propyl ester | 214 | analogously to example | 7.64% | VI.13 |
| 45 | 6-chloro-3-methyl-2-thioxo-1,2-dihydroquinoline-4-carboxylic acid propyl ester | 216 | analogously to example | 5.97% | 44 |
| 46 | 3-ethyl-2-thioxo-1,2-dihydroquinoline-4-carboxylic acid allyl ester | 178–179 | analogously to example | 5.59% | 50 |
| 47 | 3-ethyl-2-thioxo-1,2-dihydroquinoline-4-carboxylic acid benzyl ester | 176–178 | analogously to example | 5.79% | 49 |
| 48 | 3-ethyl-2-thioxo-1,2-dihydroquinoline-4-carboxylic acid 3-methylbut-2-enyl ester | 121–123 | analogously to example | 5.5% | 51 |

TABLE 3-continued

Synthesized derivatives of the formulae (1) and (1a)

| No. | Structure | m.p. (°C) | Method | Ref. |
|---|---|---|---|---|
| 49 | (3-ethyl-2-oxo-1,2-dihydroquinoline-4-carboxylic acid benzyl ester) | 174 | analogously to example 7.64% | VI.3 |
| 50 | (3-ethyl-2-oxo-1,2-dihydroquinoline-4-carboxylic acid allyl ester) | 153–154 | analogously to example 7.95% | VI.3 |
| 51 | (3-ethyl-2-oxo-1,2-dihydroquinoline-4-carboxylic acid 3-methylbut-2-enyl ester) | 101–102 | analogously to example 7.95% | VI.3 |
| 52 | (3-isobutyl-2-thioxo-1,2-dihydroquinoline-4-carboxylic acid pentan-3-yl ester) | 146–147 | analogously to example 7.48% | VI.4 |
| 53 | (6-fluoro-3-phenyl-2-thioxo-1,2-dihydroquinoline-4-carboxylic acid phenyl ester) | 238–242 | analogously to example 5.56% | 13 |
| 54 | (3-isobutyl-2-thioxo-1,2-dihydroquinoline-4-carboxylic acid pentan-3-yl ester) | 157–158 | analogously to example 5.55% | 52 |

TABLE 3-continued

Synthesized derivatives of the formulae (1) and (1a)

| | | | | |
|---|---|---|---|---|
| 55 | (structure) | 119–120 | analogously to example 7.82% | VI.4 |
| 56 | (structure) | 250–252 | analogously to example 5.68% | 12 |
| 57 | (structure) | 129–130 | analogously to example 5.82% | 55 |
| 58 | (structure) | 245–250 | analogously to example 7.36% | VI.7 |
| 59 | (structure) | 212–215 | analogously to example 7.88% | VI.12 |

TABLE 3-continued
Synthesized derivatives of the formulae (1) and (1a)
| | | | | |
|---|---|---|---|---|
| 60 | 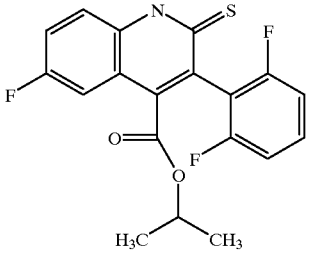 | 246–248 | analogously to example 5.58% | 58 |
| 61 | 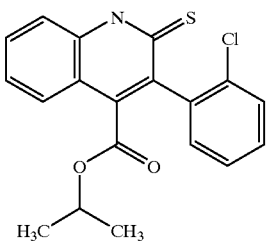 | 264–266 | analogously to example 5.49% | 59 |
| 62 | 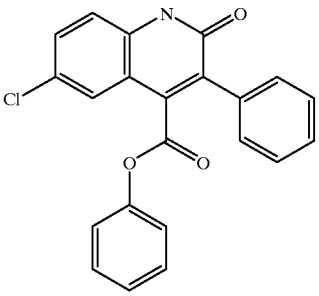 | 272–275 | analogously to example 7.61% | VI.2 |
| 63 | 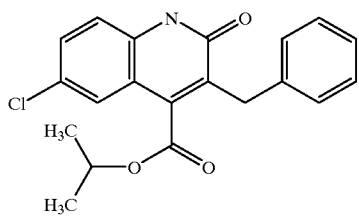 | 226 | analogously to exmaple 7.28% | VI.8 |
| 64 | 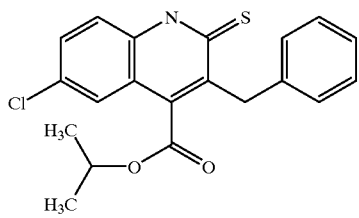 | 200 | analogously to example 5.42% | 63 |
| 65 | 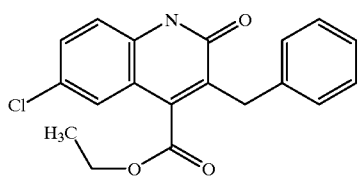 | 200 | analogously to example 7.54% | VI.8 |

TABLE 3-continued

Synthesized derivatives of the formulae (1) and (1a)

| 66 | (6-chloro-3-ethyl-2-oxo-1,2-dihydroquinoline-4-carboxylic acid ethyl ester) | 175–175 | analogously to example 7.27% | VI.14 |
| 67 | (6-chloro-3-ethyl-2-thioxo-1,2-dihydroquinoline-4-carboxylic acid ethyl ester) | 184–185 | analogously to example 5.82% | 66 |
| 68 | (6-chloro-3-ethyl-2-oxo-1,2-dihydroquinoline-4-carboxylic acid cyclohexyl ester) | 223 | analogously to example 7.5% | VI.14 |
| 69 | (6-chloro-3-ethyl-2-oxo-1,2-dihydroquinoline-4-carboxylic acid allyl ester) | 174–175 | analogously to example 7.27% | VI.14 |
| 70 | (6-chloro-3-ethyl-2-thioxo-1,2-dihydroquinoline-4-carboxylic acid cyclohexyl ester) | 184 | analogously to example 5.94% | 68 |

TABLE 3-continued

Synthesized derivatives of the formulae (1) and (1a)

| # | Structure | mp (°C) | Method | Ref |
|---|---|---|---|---|
| 71 | (6-chloro-3-ethyl-2-thioxoquinoline-4-carboxylic acid allyl ester) | 187–189 | analogously to example 5. 79% | 69 |
| 72 | (6-chloro-3-ethyl-2-thioxoquinoline-4-carboxylic acid 3-methyl-2-butenyl ester) | 141–142 | analogously to example 7. 21% | VI.14 |
| 73 | (6-chloro-3-benzyl-2-thioxoquinoline-4-carboxylic acid ethyl ester) | 209 | analogously to example 5. 56% | VI.8 |
| 74 | (6-chloro-2-(methoxyimino)-3-(4-chlorophenyl)quinoline-4-carboxylic acid isopropyl ester) | 178–180 | see Example 15. 19% | 28 |
| 75 | (6-chloro-3-benzyl-2-oxoquinoline-4-carboxylic acid 3-methylbutyl ester) | 202 | analogously to example 7. 35% | VI.8 |
| 76 | (6-chloro-3-benzyl-2-thioxoquinoline-4-carboxylic acid 3-methylbutyl ester) | 160 | analogously to example 5. 35% | 75 |

TABLE 3-continued

Synthesized derivatives of the formulae (1) and (1a)

| | | | | | |
|---|---|---|---|---|---|
| 77 | 6-Cl, 8-CH₃, 3-CH₃, 4-CO₂CH(CH₃)₂, 2-oxo quinoline | 214 | analogously to example | 7.56% | VI.22 |
| 78 | 6-Cl, 8-CH₃, 3-CH₃, 4-CO₂CH(CH₃)₂, 2-thioxo quinoline | 187 | analogously to example | 5.95% | 77 |
| 79 | 6-Cl, 8-CH₃, 3-CH₃, 4-CO₂CH₂CH=C(CH₃)₂... 2-oxo quinoline | 179 | analogously to example | 7.70% | VI.22 |
| 80 | 6-Cl, 8-CH₃, 3-CH₃, 4-CO₂CH₂CH=C(CH₃)₂... 2-thioxo quinoline | 125 | analogously to example | 5.83% | 79 |
| 81 | 6-OCH₃, 3-phenyl, 4-CO₂CH(CH₃)₂, 2-oxo quinoline | 231 | see Example | 13.60% | VI.21 |

TABLE 3-continued

Synthesized derivatives of the formulae (1) and (1a)

| | | | | |
|---|---|---|---|---|
| 82 | 6-methoxy-3-phenyl-2-thioxo-1,2-dihydroquinoline-4-carboxylic acid isopropyl ester | 219 | see Example 14. 79% | 81 |
| 83 | 6-methoxy-2-oxo-3-phenyl-1,2-dihydroquinoline-4-carboxylic acid propyl ester | 229 | analogously to example 7. 72% | VI.21 |
| 84 | 6-methoxy-3-phenyl-2-thioxo-1,2-dihydroquinoline-4-carboxylic acid propyl ester | 224 | analogously to example 5. 53% | 83 |
| 85 | 6-fluoro-3-phenyl-2-thioxo-1,2-dihydroquinoline-4-carboxylic acid methyl ester | 227–228 | analogously to example 5. 15% | 10 |
| 86 | 6-chloro-3-(2-methoxyphenyl)-2-oxo-1,2-dihydroquinoline-4-carboxylic acid isopropyl ester | 220–223 | analogously to example 7. 55% | VI.16 |
| 87 | 6-chloro-3-(4-methoxyphenyl)-2-oxo-1,2-dihydroquinoline-4-carboxylic acid isopropyl ester | 230–232 | analogously to example 7. 64% | VI.18 |

TABLE 3-continued

Synthesized derivatives of the formulae (1) and (1a)

| No. | Structure | m.p. (°C) | Method | Starting material |
|---|---|---|---|---|
| 88 | | 194–195 | analogously to example 7.78% | VI.9 |
| 89 | | 210–212 | analogously to example 5.65% | 88 |
| 90 | | 228–230 | analogously to example 5.63% | 87 |
| 91 | | 251–254 | analogously to example 5.40% | 86 |
| 92 | | 154 | analogously to example 5.57% | 72 |
| 93 | | 148 | analogously to example 7.58% | VI.19 |
| 94 | | 144 | analogously to example 7.61% | VI.19 |

TABLE 3-continued

Synthesized derivatives of the formulae (1) and (1a)

| # | Structure | mp (°C) | Method / Yield | Ref |
|---|---|---|---|---|
| 95 | 6-F, 3-ethyl, 4-CO-O-allyl, 2-thioxoquinoline | 183 | analogously to example 5. 82% | 93 |
| 96 | 6-F, 3-ethyl, 4-CO-O-isopropyl, 2-thioxoquinoline | 184 | analogously to example 5. 98% | 94 |
| 97 | 6-Br, 3-ethyl, 4-CO-O-allyl, 2-oxoquinoline | 187 | analogously to example 7. 75% | VI.20 |
| 98 | 3-ethyl, 4-CO-O-cyclopentyl, 2-oxoquinoline | 155–156 | analogously to example 7. 46% | VI.3 |
| 99 | 6-Cl, 3-phenyl, 4-CO-ethyl, 2-oxoquinoline | 230–233 | analogously to example 16. 19% | VI.2 |
| 100 | 6-Cl, 3-phenyl, 4-CO-phenyl, 2-oxoquinoline | 266–267 | see Example 16, 13% | VI.2 |

TABLE 3-continued

Synthesized derivatives of the formulae (1) and (1a)

| 101 | | 180–182 | analogously to example 16.14% | VI.2 |

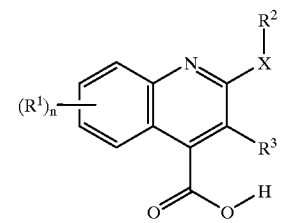

VI and its tautomeric form, of the formula VIa

VIa

Table 4 gives an overview of all quinoline-4-carboxylic acids synthesized hitherto.

TABLE 4

| Designation | R(1) | R(2) | R(3) | X | Preparation method Yield |
|---|---|---|---|---|---|
| VI.1 | H | H | phenyl | O | see Example 6; 74% |
| VI.2 | 6-Cl | H | phenyl | O | analogously to Example 6, 43% |
| VI.3 | H | H | ethyl | O | analogously to Example 9, 36% |
| VI.4 | H | H | isobutyl | O | analogously to Example 9, 48% |
| VI.5 | 6-F | H | phenyl | O | analogously to Example 6, 91% |
| VI.6 | H | H | ethenyl | O | analogously to Example 1, 16% |
| VI.7 | 6-F | H | 2,6-F$_2$-phenyl | O | analogously to Example 6, 8% |
| VI.8 | 6-Cl | H | benzyl | O | analogously to Example 1, 13% |
| VI.9 | 6-CF$_3$O | H | phenyl | O | analogously to Example 6, 99% |
| VI.10 | H | H | methyl | O | analogously to Example 1, 17% |
| VI.11 | H | H | isopropyl | O | analogously to Example 1, 26% |
| VI.12 | H | H | 2-Cl-phenyl | O | analogously to Example 6, 80% |
| VI.13 | 6-Cl | H | methyl | O | see Example 1; 74% |
| VI.14 | 6-Cl | H | ethyl | O | see Example 9, 42% |
| VI.15 | 6-Cl | H | 4-Cl-phenyl | O | analogously to Example 6, 75% |
| VI.16 | 6-Cl | H | 2-CH$_3$O-phenyl | O | analogously to Example 6, 99% |
| VI.17 | 6-Cl | H | 3-CH$_3$O-phenyl | O | analogously to Example 6, 47% |
| VI-18 | 6-Cl | H | 4-CH$_3$O-phenyl | O | analogously to Example 6, 67% |
| VI.19 | 6-F | H | ethyl | O | analogously to Example 9, 13% |
| VI.20 | 6-Br | H | ethyl | O | analogously to Example 1, 12% |
| VI.21 | 6-CH$_3$O | H | phenyl | O | analogously to Example 6, 74% |
| VI.22 | 6-Cl-8-CH$_3$ | H | CH$_3$ | O | analogously to Example 1, 27% |

The indole derivatives used as starting materials for the preparation of the quinolinecarboxylic acids can be prepared by the methods of examples I–III.

What is claimed is:
1. A compound of the formula I

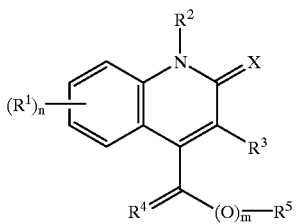
(I)

or a tautomeric form thereof, of the formula Ia

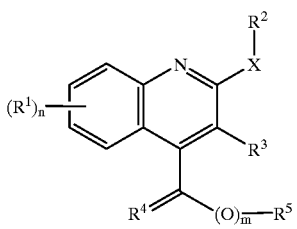
(Ia)

in which:
I) n is zero, one, two, three, or four,
the individual substituents $R^1$ independently of one another are fluorine, chlorine, bromine, iodine, trifluoromethyl, trifluoromethoxy, hydroxyl, alkyl, cycloalkyl, alkoxy, alkoxy(alkoxy), alkylthio, alkylsulfinyl, alkylsulfonyl, nitro, amino, azido, alkylamino, dialkylamino, piperidino, morpholino, 1-pyrrolidinyl, acyl, acyloxy, acylamino, cyano, carbamoyl, carboxyl, alkyloxycarbonyl, hydroxysulfonyl, sulfamoyl, or a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, heteroaroyl, heteroaryl or heteroarylmethyl radical, each of which is unsubstituted or substituted by up to five radicals $R^6$ which are independent of one another, where $R^6$ is
fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, alkyloxycarbonyl, phenyl, phenoxy or heteroaryl, X is oxygen, sulfur, selenium or substituted nitrogen $N-R^2$, $N-O-R^2$, in which $R^2$ has the meanings given below, and $R^2$ is hydrogen,
alkyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
alkenyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
alkynyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
cycloalkyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
(cycloalkenyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
(cycloalkyl)-(alkyl), which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
(cycloalkenyl)-(alkyl), which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
alkylcarbonyl, which is unsubstituted or substituted by fluorine, chlorine , bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
alkenylcarbonyl, which is unsubstituted or substituted by fluorine, chlorine or hydroxyl, alkoxy, oxo, phenyl;
(cycloalkyl) carbonyl, which is unsubstituted or substituted by fluorine, chlorine or hydroxyl, alkoxy, oxo, phenyl;
(cycloalkenyl)carbonyl, which is unsubstituted or substituted by fluorine, chlorine or hydroxyl, alkoxy, oxo, phenyl;
(cycloalkyl)-(alkyl)carbonyl, which is unsubstituted or substituted by fluorine, chlorine or hydroxyl, alkoxy, oxo, phenyl;
(cycloalkenyl)-(alkyl)carbonyl, which is unsubstituted or substituted by fluorine, chlorine or hydroxyl, alkoxy, oxo, phenyl;
alkyloxycarbonyl, which is unsubstituted or substituted by fluorine, chlorine, bromine, hydroxyl, alkoxy, alkylamino, dialkylamino, alkylthio;
alkenyloxycarbonyl, which is unsubstituted or substituted by fluorine, chlorine, hydroxyl, alkoxy, oxo, phenyl;
alkynyloxycarbonyl, which is unsubstituted or substituted by fluorine, chlorine, hydroxyl, alkoxy, oxo, phenyl;
alkylthiocarbonyl, which is unsubstituted or substituted by fluorine, chlorine, hydroxyl, alkoxy, oxo, phenyl;
alkenylthiocarbonyl, which is unsubstituted or substituted by fluorine, chlorine, hydroxyl, alkoxy, oxo, phenyl;

alkylamino- or dialkylaminocarbonyl, each of which is unsubstituted or substituted by fluorine, chlorine, hydroxyl, alkoxy, oxo, phenyl;

alkenylamino- or dialkenylaminocarbonyl, each of which is unsubstituted or substituted by fluorine, chlorine, hydroxyl, alkoxy, oxo, phenyl;

alkylsulfonyl, which is unsubstituted or substituted by fluorine, chlorine, hydroxyl, alkoxy, alkylthio, oxo, phenyl;

alkenylsulfonyl, which is unsubstituted or substituted by fluorine, chlorine, hydroxyl, alkoxy, oxo, phenyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, aralkynyl, arylalkylcarbonyl, arylalkenylcarbonyl, arylalkoxycarbonyl, each of which is unsubstituted or substituted by up to five radicals $R^6$ which are independent of one another, where $R^6$ is as defined above;

or heteroaryl, heteroarylalkyl, heteroarylalkenyl, heteroarylalkylcarbonyl or heteroarylalkenylcarbonyl, each of which is substituted by up to three radicals $R^6$ which are independent of one another, where $R^6$ is as defined above, and $R^3$ is hydrogen, alkyl, which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

alkenyl, which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkyl, which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkenyl, which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

or aryl, arylalkyl, heteroaryl or heteroarylalkyl, each of which is unsubstituted or substituted by up to five radicals $R^6$ which are independent of one another, where $R^6$ is as defined above, and $R^4$ is oxygen, sulfur, $NOR^2$, NOH, where $R^2$ is as defined above, or $R^4$ is an alkyl radical bonded via a double bond, which is unsubstituted or substitute by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl, or $R^4$ is two hydrogen atoms residing on the linking carbon atom, where in this case $R^5$ additionally to the definitions indicated below for $R^5$ this radical can also be hydrogen or alkylcarbonyl, and in which m is 1, and $R^5$ is alkyl, which is substituted by at least one fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkenyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkynyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkenyl, which is unsubstituted or substituted by fluorine, chlorine, bromine, iodine cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

(cycloalkyl)-(alkyl), which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

(cycloalkenyl)-(alkyl), which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

or arylalkyl, arylalkenyl, arylalkynyl, each of which is unsubstituted or substituted by up to five radicals $R^6$ which are independent of one another, where $R^6$ is as defined above;

or aryl which is substituted by up to five radicals $R^6$ which are independent of one another, where $R^6$ is defined above, or heteroaryl, heteroarylalkyl, heteroarylalkenyl, which is unsubstituted or substituted by up to three radicals $R^6$ which are independent of one another, where $R^6$ is as defined above, or an optical isomer, a diastereomer in pure form, or a mixture of diastereomers in pure form, or an addition salt thereof, with the exception of a compound of the formula I in which the radicals $R^1, R^2, R^3, R^4, R^5$, X and m simultaneously have the following meanings:

$R^2$ is hydrogen, $R^3$ is phenyl, which is unsubstituted or substituted as indicated above, X is oxygen, $R^4$ is oxygen, m is 1 and $R^5$ is $C_1$–$C_6$-alkyl furthermore with the exception of a compound of the formula I in which $R^1$ and $R^2$ are hydrogen, $R^3$ is hydrogen, methyl or ethyl, $R^4$ is oxygen and $R^5$ is methyl, furthermore with the exception of a compound of the formula I in which $R^1$ is hydrogen, $R^2$ is $C_1$–$C_4$-alkyl, $R^3$ is phenyl, which is unsubstituted or substituted as indicated above, $R^4$ is 0, m is 1, X is 0 and $R^5$ is methyl, ethyl, furthermore with the exception of a compound of the formula I in which $R^1$ and $R^2$ are hydrogen, $R^3$ is ethenyl, $R^4$ is 0, m is 1, X is 0 and $R^5$ is methyl, ethyl, and furthermore with the exception of a compound of the formula Ia in which $R^1$ and $R^2$ are hydrogen, $R^3$ is ethyl, $R^4$ is 0, m is 1, X is 0 and $R^5$ is methyl.

2. A compound of the formula I or Ia as claimed in claim 1, in which n is zero, one, two, or three, the individual substituents $R^1$ independently of one another are fluorine, chlorine, bromine, iodine, trifluoromethyl, trifluoromethoxy, hydroxyl, ($C_1$–$C_{10}$)-alkyl, ($C_3$–$C_8$)-cycloalkyl, ($C_1$–$C_{10}$)-alkoxy, ($C_1$–$C_{10}$)-alkoxy(($C_1$–$C_{10}$)-alkoxy), ($C_1$–$C_{10}$)-alkylthio, ($C_1$–$C_{10}$)-alkylsulfinyl, ($C_1$–$C_{10}$)-alkylsulfonyl, nitro, amino, azido, ($C_1$–$C_{10}$)-alkylamino, ($C_1$–$C_{10}$)-dialkylamino, piperidino, morpholino, 1-pyrrolidinyl, ($C_1$–$C_{10}$)-acyl, ($C_1$–$C_{10}$)-acyloxy, ($C_1$–$C_{10}$)-acylamino, cyano, carbamoyl, carboxyl, ($C_1$–$C_{10}$)-alkyloxycarbonyl, hydroxysulfonyl, sulfamoyl, or a phenyl, phenoxy, phenoxycarbonyl, phenylthio, phenylsulfinyl, phenylsulfonyl, phenoxysulfonyl, phenylsulfonyloxy, phenylsulfonylamino, benzoyl, heteroaroyl, heteroaryl or heteroarylmethyl radical, each of which is unsubstituted or substituted by up to five radicals $R^6$ which are independent of one another, where $R^6$ is fluorine, chlorine, bromine, iodine, cyano, trifluoromethyl, trifluoromethoxy, nitro, amino, azido, ($C_1$–$C_6$)-alkyl, ($C_3$–$C_8$)-cycloalkyl, ($C_1$–$C_6$)-alkoxy, ($C_1$–$C_6$)-alkylthio, ($C_1$–$C_6$)-alkylsulfinyl, ($C_1$–$C_6$)-alkylsulfonyl, ($C_1$–$C_6$)-alkylamino, ($C_1$–$C_6$)-dialkylamino, ($C_1$–$C_6$)-alkyloxycarbonyl, phenyl, phenoxy or heteroaryl, X is oxygen, sulfur or substituted nitrogen N—$R^2$, N—O—$R^2$, in which $R^2$ has the meanings, given below, and $R^2$ is hydrogen, ($C_1$–$C_{12}$)-alkyl, which is unsubstituted or substituted by fluorine, chlorine, bromine, iodine, cyano, amino, mercapto, hydroxyl, ($C_1$–$C_6$)-acyloxy, benzoyloxy, benzyloxy, phenoxy, ($C_1$–$C_4$)-alkoxy, ($C_1$–$C_4$)-alkylamino, ($C_1$–$C_4$)-dialkylamino, ($C_1$–$C_4$)-alkylthio, ($C_1$–$C_4$)-alkylsulfonyl, phenylsulfonyl, oxo, carboxyl, carbamoyl;

($C_2$–$C_{12}$)-alkenyl, which is unsubstituted or substituted by fluorine, chlorine, bromine, iodine, cyano, amino, mercapto, hydroxyl, acyloxy, benzoyloxy, benzyloxy, phenoxy, ($C_1$–$C_4$)-alkoxy, ($C_1$–$C_4$)-alkylamino, ($C_1$–$C_4$)-dialkylamino, ($C_1$–$C_4$)-alkylthio, ($C_1$–$C_4$)-alkylsulfonyl, phenylsulfonyl, oxo, thioxo, carboxyl, carbamoyl;

($C_2$–$C_8$)-alkynyl, which is unsubstituted or substituted by fluorine, chlorine, bromine, iodine, cyano, amino, mercapto, hydroxyl, acyloxy, benzoyloxy, benzyloxy, phenoxy, ($C_1$–$C_4$)-alkoxy, ($C_1$–$C_4$)-alkylamino, ($C_1$–$C_4$)-dialkylamino;

($C_1$–$C_6$)-alkylcarbonyl, which is unsubstituted or substituted by fluorine, chlorine, bromine, iodine, cyano, amino, mercapto, hydroxyl, ($C_1$–$C_4$)-acyloxy, benzoyloxy, benzyloxy, phenoxy, ($C_1$–$C_4$)-alkoxy, ($C_1$–$C_4$)-alkylamino, ($C_1$–$C_4$)-dialkylamino, ($C_1$–$C_4$)-alkylthio, ($C_1$–$C_4$)-alkylsulfonyl, phenylsulfonyl, oxo, thioxo, carboxyl, carbamoyl;

($C_2$–$C_6$)-alkenylcarbonyl, which is unsubstituted or substituted by fluorine, chlorine or hydroxyl, ($C_1$–$C_4$)-alkoxy, oxo, phenyl;

($C_3$–$C_6$)-(cycloalkyl)carbonyl, which is unsubstituted or substituted by fluorine, chlorine or hydroxyl, ($C_1$–$C_4$)-alkoxy, oxo, phenyl;

($C_3$–$C_6$)-(cycloalkenyl)carbonyl, which is unsubstituted or substituted by fluorine, chlorine or hydroxyl, ($C_1$–$C_4$)-alkoxy, oxo, phenyl;

($C_3$–$C_6$)-(cycloalkyl)-(($C_1$–$C_4$)-alkyl)carbonyl, which is unsubstituted or substituted by fluorine, chlorine or hydroxyl, ($C_1$–$C_4$)-alkoxy, oxo, phenyl;

($C_3$–$C_6$)-(cycloalkenyl)-((C-$C_4$)-alkyl)carbonyl, which is unsubstituted or substituted by fluorine, chlorine or hydroxyl, ($C_1$–$C_4$)-alkoxy, oxo, phenyl;

($C_1$–$C_6$)-alkyloxycarbonyl, which is unsubstituted or substituted by fluorine, chlorine, bromine, hydroxyl, ($C_1$–$C_4$)-alkoxy, ($C_1$–$C_4$)-alkylamino, ($C_1$–$C_4$)-dialkylamino, ($C_1$–$C_4$)-alkylthio;

($C_2$–$C_6$)-alkenyloxycarbonyl, which is unsubstituted or substituted by fluorine, chlorine, hydroxyl, ($C_1$–$C_4$)-alkoxy, oxo, phenyl;

($C_1$–$C_6$)-alkylamino- or ($C_1$–$C_6$)-dialkylaminocarbonyl, which are unsubstituted or substituted by fluorine, chlorine, hydroxyl, ($C_1$–$C_4$)-alkoxy, oxo, phenyl;

or phenyl, phenylcarbonyl, phenyloxycarbonyl, phenylsulfonyl, phenyl-($C_1$–$C_2$)-alkyl, phenyl-($C_1$–$C_2$)-alkylcarbonyl, each of which is unsubstituted or substituted by up to five radicals $R^6$ which are independent of one another, where $R^6$ is as defined above;

or heteroaryl, heteroaryl-($C_1$–$C_2$)-alkyl or heteroaryl-($C_1$–$C_2$)-alkylcarbonyl, each of which is substituted by up to two radicals $R^6$ which are independent of one another, where $R^6$ is as defined above, and $R^3$ is ($C_1$–$C_{15}$)-alkyl, which is unsubstituted or substituted by fluorine, chlorine, hydroxyl, amino, mercapto, ($C_1$–$C_6$)-acyloxy, benzoyloxy, benzyloxy, phenoxy, ($C_1$–$C_6$)-alkoxy, ($C_1$–$C_6$)-alkylamino, ($C_1$–$C_6$)- dialkylamino, $(C_1-C_6)$-alkylthio, $(C_1-C_6)$-alkylsulfonyl, $(C_1-C_6)$-alkylsulfinyl, carboxyl, carbamoyl;

$(C_2-C_{12})$-alkenyl, which is unsubstituted or substituted by fluorine, chlorine, hydroxyl, amino, mercapto, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, $(C_1-C_6)$-alkylsulfinyl, carboxyl, carbamoyl;

$(C_3-C_8)$-cycloalkyl, which is unsubstituted or substituted by fluorine, chlorine, hydroxyl, amino, mercapto, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, $(C_1-C_6)$-alkylsulfinyl, carboxyl, carbamoyl;

$(C_3-C_8)$-cycloalkenyl, which is unsubstituted or substituted by fluorine, chlorine, hydroxyl, amino, mercapto, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, $(C_1-C_6)$-alkylsulfinyl, carboxyl, carbamoyl;

or aryl, aryl-$(C_1-C_4)$-alkyl, heteroaryl or heteroaryl-$(C_1-C_4)$-alkyl, each of which is unsubstituted or substituted by up to five radicals $R^6$ which are independent of one another, where $R^6$ is as defined above, and $R^4$ is oxygen, $NOR^2$, NOH, where $R^2$ is as defined above, or $R^4$ is a $(C_1-C_{10})$-alkyl radical bonded via a double bond, which is unsubstituted or substituted by fluorine, chlorine, hydroxyl, amino, mercapto, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, $(C_1-C_4)$-alkylsulfinyl, carboxyl, carbamoyl;

and m is 1, and $R^5$ is $(C_1-C_{15})$-alkyl, which is unsubstituted or substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

$(C_2-C_{12})$-alkenyl, which is unsubstituted or substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

$(C_2-C_{10})$-alkynyl, which is unsubstituted or substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

$(C_3-C_{10})$-cycloalkyl, which is unsubstituted or substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

$(C_3-C_{10})$-cycloalkenyl, which is unsubstituted or substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

$(C_3-C_{10})$-(cycloalkyl)-$((C_1-C_4)$-alkyl), which is unsubstituted or substituted by fluorine, chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

$(C_3-C_{10})$-(cycloalkenyl)-$(C_1-C_4)$-(alkyl), which is unsubstituted or substituted by fluorine chlorine, bromine, iodine, cyano, amino, mercapto, hydroxyl, $(C_1-C_6)$-acyloxy, benzoyloxy, benzyloxy, phenoxy, $(C_1-C_6)$-alkoxy, $(C_1-C_6)$-alkylamino, $(C_1-C_6)$-dialkylamino, $(C_1-C_6)$-alkylthio, $(C_1-C_6)$-alkylsulfonyl, phenylsulfonyl, oxo, thioxo, carboxyl, carbamoyl;

or aryl-$(C_1-C_4)$-alkyl, aryl-$(C_2-C_4)$-alkenyl, aryl-$(C_2-C_4)$-alkynyl, each of which is unsubstituted or substituted by up to five radicals $R^6$ which are independent of one another, where $R^6$ is as defined above;

or aryl which is substituted by up to five radicals $R^6$ which are independent of one another, where $R^6$ is defined above, or heteroaryl, heteroaryl-$(C_1-C_4)$-alkyl, each of which is unsubstituted or substituted by up to three radicals $R^6$ which are independent of one another, where $R^6$ is as defined above, or an optical isomer, a diastereomer in pure form, or a mixture of diastereomers in pure form, or an addition salt thereof.

3. A compound of the formula I or Ia as claimed in claim 1, in which n is zero, one, or two, the individual substituents $R^1$ independently of one another are fluorine, chlorine, bromine, iodine, trifluoromethyl, trifluoromethoxy, hydroxyl, $(C_1-C_8)$-alkyl, $(C_3-C_8)$-cycloalkyl, $(C_1-C_8)$-alkoxy, $(C_1-C_8)$-alkoxy$((C_1-C_8)$-alkoxy), $(C_1-C_8)$-alkylthio, $(C_1-C_8)$-alkylsulfinyl, $(C_1-C_8)$-alkylsulfonyl, nitro, amino, azido, $(C_1-C_8)$-acyl, $(C_1-C_8)$-acyloxy, cyano, carbamoyl, carboxyl, $(C_1-C_8)$-alkyloxycarbonyl, sulfamoyl, or a phenyl, phenoxy, phenoxycarbonyl, phenylthio, phenylsulfinyl, phenylsulfonyl, phenoxysulfonyl, phenylsulfonyloxy, phenylsulfonylamino or benzoyl radical, each of which is unsubstituted or substituted by up to two radicals $R^6$ which are independent of one another, where $R^6$ is fluorine, chlorine, bromine, iodine, cyano, trifluoromethyl, trifluoromethoxy, nitro, amino, azido, $(C_1-C_4)$-alkyl, $(C_3-C_6)$-cycloalkyl, $(C_1-C_4)$-alkoxy, $(C_1-C_4)$-alkylthio, $(C_1-C_4)$-alkylsulfinyl, $(C_1-C_4)$-alkylsulfonyl, X is oxygen, sulfur or substituted nitrogen $N-R^2$, $N-O-R^2$, in which $R^2$ has one of the meanings given below, and $R^2$ is hydrogen, $(C_1-C_8)$-alkyl, which is unsubstituted or substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, carboxyl, carbamoyl;

$(C_2-C_8)$-alkenyl, which is unsubstituted or substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl; and $R^3$ is
- $(C_1-C_{10})$-alkyl, which is unsubstituted or substituted by fluorine, chlorine, hydroxyl, amino, mercapto, $(C_1-C_6)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, $(C_1-C_4)$-alkylsulfinyl, carboxyl, carbamoyl;
- $(C_2-C_8)$-alkenyl, which is unsubstituted or substituted by fluorine, chlorine, hydroxyl, amino, mercapto, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, $(C_1-C_4)$-alkylsulfinyl, carboxyl, carbamoyl;
- $(C_3-C_8)$-cycloalkyl, which is unsubstituted or substituted by fluorine, chlorine, hydroxyl, amino, mercapto, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, $(C_1-C_4)$-alkylsulfinyl, carboxyl, carbamoyl;
- $(C_3-C_6)$-cycloalkenyl, which is unsubstituted or substituted by fluorine, chlorine, hydroxyl, amino, mercapto, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, $(C_1-C_4)$-alkylsulfinyl, carboxyl, carbamoyl;
- or aryl, aryl-$(C_1-C_2)$-alkyl, heteroaryl or heteroaryl-$(C_2-C_4)$-alkyl, each of which is unsubstituted or substituted by up to two radicals $R^6$ which are independent of one another, where $R^6$ is as defined above, and $R^4$ is oxygen,
and m is 1,
and $R^5$ is
- $(C_1-C_{10})$-alkyl, which is unsubstituted or substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_2-C_{10})$-alkenyl, which is unsubstituted or substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_2-C_8)$-alkynyl, which is unsubstituted or substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_3-C_8)$-cycloalkyl, which is unsubstituted or substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_3-C_8)$-cycloalkenyl, which is unsubstituted or substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_3-C_8)$-(cycloalkyl)-($(C_1-C_3)$-alkyl), which is unsubstituted or substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- $(C_3-C_8)$-(cycloalkenyl)-($(C_1-C_3)$-alkyl), which is unsubstituted or substituted by fluorine, chlorine, bromine, iodine, cyano, amino, mercapto, hydroxyl, $(C_1-C_4)$-acyloxy, benzoyloxy, benzyloxy, phenoxy, $(C_1-C_4)$-alkoxy, $(C_1-C_4)$-alkylamino, $(C_1-C_4)$-dialkylamino, $(C_1-C_4)$-alkylthio, $(C_1-C_4)$-alkylsulfonyl, phenylsulfonyl, oxo, thioxo, carboxyl, carbamoyl;
- or aryl-$(C_1-C_4)$-alkyl, aryl-$(C_2-C_4)$-alkenyl, aryl-$(C_1-C_4)$-alkynyl, each of which is unsubstituted or substituted by up to two radicals $R^6$ which are independent of one another, where $R^6$ is as defined above;
- or aryl which is substituted by up to five radicals $R^6$ which are independent of on another, where $R^6$ is defined above,
- or heteroaryl, heteroaryl-$(C_1-C_4)$-alkyl, each of which is unsubstituted or substituted by up to three radicals $R^6$ which are independent of one another, where $R^6$ is as defined above,
- or an optical isomer, a diastereomer in pure form, or a mixture of diastereomers in pure form or an addition salt thereof.

4. A compound of the formula I or Ia as claimed in claim 1, in which n is zero, one or two,
the individual substituents $R^1$ independently of one another are fluorine, chlorine, bromine, trifluoromethyl, trifluoromethoxy, $(C_1-C_6)$-alkyl, $(C_3-C_6)$-cycloalkyl, $(C_1-C_6)$-alkoxy, $(C_1-C_6)$-alkoxy($(C_1-C_6)$-alkoxy), $(C_1-C_6)$-alkylthio, $(C_1-C_6)$-alkylsulfinyl, $(C_1-C_6)$-acyl, $(C_1-C_6)$-acyloxy, carboxyl, $(C_1-C_6)$-alkyloxycarbonyl, or
a phenyl, phenoxy, phenoxycarbonyl, phenylthio, phenylsulfonyl, phenoxysulfonyl, phenylsulfonyloxy, phenylsulfonylamino or benzoyl radical, each of which is unsubstituted or substituted by up to two radicals $R^6$ which are independent of one another,
where $R^6$ is
fluorine, chlorine, bromine, trifluoromethyl, trifluoromethoxy, azido, $(C_1-C_4)$-alkyl, $(C_4-C_6)$-cycloalkyl, $(C_1-C_4)$-alkoxy, $(C_1-C_4)$-alkylthio,
X is oxygen, sulfur or substituted nitrogen N—$R^2$, N—O—$R^2$, in which $R^2$ has the meanings given below, and $R^2$ is hydrogen,
- $(C_1-C_4)$-alkyl, which is unsubstituted or substituted by fluorine, chlorine, bromine, $(C_1-C_3)$-acyloxy, benzoyloxy, benzyloxy, phenoxy, $(C_1-C_3)$-alkoxy, phenylsulfonyl, oxo, carboxyl, carbamoyl;
- $(C_2-C_6)$-alkenyl, which is unsubstituted or substituted by fluorine, chlorine, bromine, $(C_1-C_3)$-acyloxy, benzoyloxy, benzyloxy, phenoxy, $(C_1-C_3)$-alkoxy, phenylsulfonyl, oxo, carboxyl, carbamoyl; and $R^3$ is
- $(C_1-C_8)$-alkyl, which is unsubstituted or substituted by fluorine, chlorine, hydroxyl, amino, $(C_1-C_4)$-acyloxy, benzoyloxy, benzyloxy, phenoxy, $(C_1-C_4)$-alkoxy, carboxyl;
- $(C_2-C_6)$-alkenyl, which is unsubstituted or substituted by fluorine, chlorine, hydroxyl, amino, $(C_1-C_4)$-acyloxy, benzoyloxy, benzyloxy, phenoxy, $(C_1-C_4)$-alkoxy, carboxyl;
- $(C_3-C_6)$-cycloalkyl, which is unsubstituted or substituted by fluorine, chlorine, hydroxyl, amino, $(C_1-C_4)$-acyloxy, benzoyloxy, benzyloxy, phenoxy, $(C_1-C_4)$-alkoxy, carboxyl;
- $(C_3-C_6)$-cycloalkenyl, which is unsubstituted or substituted by fluorine, chlorine, hydroxyl, amino, $(C_1-C_4)$-acyloxy, benzoyloxy, benzyloxy, phenoxy, $(C_1-C_4)$-alkoxy, carboxyl;
- or aryl, aryl-$(C_1-C_2)$-alkyl, each of which is unsubstituted or substituted by up to two radicals $R^6$ which are independent of one another, where $R^6$ is as defined above, and $R^4$ is oxygen, and m is 1, and $R^5$ is
- $(C_1-C_8)$-alkyl, which is unsubstituted or substituted by fluorine, chlorine, bromine, cyano, amino, hydroxyl, $(C_1-C_4)$-acyloxy, benzoyloxy, benzyloxy, phenoxy, $(C_1-C_4)$-alkoxy, oxo, carboxyl, carbamoyl;
- $(C_2-C_8)$-alkenyl, which is unsubstituted or substituted by fluorine, chlorine, bromine, iodine, cyano, amino, hydroxyl, $(C_1-C_4)$-acyloxy, benzoyloxy, benzyloxy, phenoxy, $(C_1-C_4)$-alkoxy, oxo, carboxyl, carbamoyl;
- $(C_2-C_6)$-alkynyl, which is unsubstituted or substituted by fluorine, chlorine, bromine, cyano, amino, hydroxyl, $(C_1-C_4)$-acyloxy, benzoyloxy, benzyloxy, phenoxy, $(C_1-C_4)$-alkoxy, oxo, carboxyl, carbamoyl;
- $(C_3-C_6)$-cycloalkyl, which is unsubstituted or substituted by fluorine, chlorine, bromine, cyano, amino, hydroxyl, $(C_1-C_4)$-acyloxy, benzoyloxy, benzyloxy, phenoxy, $(C_1-C_4)$-alkoxy, oxo, carboxyl, carbamoyl;
- $(C_3-C_6)$-cycloalkenyl, which is unsubstituted or substituted by fluorine, chlorine, bromine, amino, hydroxyl, $(C_1-C_4)$-acyloxy, benzoyloxy, benzyloxy, phenoxy, $(C_1-C_4)$-alkoxy;
- $(C_3-C_6)$-(cycloalkyl)-$((C_1-C_2)$-alkyl), which is unsubstituted or substituted by fluorine, chlorine, bromine, amino, hydroxyl, $(C_1-C_4)$-acyloxy, benzoyloxy, benzyloxy, phenoxy;
- $(C_3-C_6)$-(cycloalkenyl)-$((C_1-C_2)$-alkyl), which is unsubstituted or substituted by fluorine, chlorine, bromine, amino, hydroxyl, $(C_1-C_4)$-acyloxy, benzoyloxy, benzyloxy, phenoxy;
- or aryl-$(C_1-C_4)$-alkyl, aryl-$(C_2-C_4)$-alkenyl, each of which is unsubstituted or substituted by up to two radicals $R^6$ which are independent of one another, where $R^6$ is as defined above;
- or aryl which is substituted by up to five radicals $R^6$ which are independent of on another, where $R^6$ is defined above,
- or heteroaryl, heteroaryl-$(C_1-C_4)$-alkyl, each of which is unsubstituted or substituted by up to three radicals $R^6$ which are independent of one another, where $R^6$ is as defined above,
- or an optical isomer, a diastereomer in pure form, or a mixture of diastereomers in pure form, or an addition salt thereof.

5. A compound of the formula I or Ia as claimed in claim 1, in which n is zero, or one, the substituent $R^1$ is fluorine, chlorine, bromine, trifluoromethyl, trifluoromethoxy, $(C_5-C_6)$-cycloalkyl, $(C_1-C_4)$-alkoxy, $(C_1-C_4)$-alkoxy$((C_1-C_4)$-alkoxy), $(C_1-C_4)$-alkylthio, $(C_1-C_4)$-acyl, or a phenyl, phenoxy or benzoyl radical each of which is unsubstituted or substituted by a radical $R^6$, where $R^6$ is
- fluorine, chlorine, bromine, trifluoromethyl, trifluoromethoxy, $(C_1-C_4)$-alkyl, $(C_1-C_4)$-alkoxy, $(C_1-C_4)$-alkylthio, X is oxygen or sulfur, and $R^2$ is hydrogen, and $R^3$ is
- $(C_1-C_6)$-alkyl;
- $(C_2-C_6)$-alkenyl;
- $(C_3-C_6)$-cycloalkyl;
- or phenyl, benzyl, each of which is unsubstituted or substituted by up to two radicals $R^6$ which are independent of one another, where $R^6$ is as defined above, and $R^4$ is oxygen, and m is 1, and $R^5$ is
- $(C_1-C_6)$-alkyl, which is unsubstituted or substituted by fluorine, chlorine, bromine, cyano, amino, hydroxyl, $(C_1-C_4)$-acyloxy, benzoyloxy, benzyloxy, phenoxy, $(C_1-C_4)$-alkoxy;
- $(C_2-C_6)$-alkenyl, which is unsubstituted or substituted by fluorine, chlorine, bromine, amino, hydroxyl, $(C_1-C_4)$-acyloxy, carboxyl;
- $(C_3-C_6)$-cycloalkyl;
- $(C_3-C_6)$-cycloalkenyl;
- $(C_3-C_6)$-(cycloalkyl)-$((C_1-C_2)$-alkyl);
- or aryl-$(C_1-C_4)$-alkyl, each of which is unsubstituted or substituted by up to two radicals $R^6$ which are independent of one another, where $R^6$ is as defined above,
- or aryl which is substituted by up to five radicals $R^6$ which are independent of one another, where $R^6$ is defined above,
- or an optical isomer, a diastereomer in pure form, or a mixture of diastereomers in pure form, or an addition salt thereof.

6. A method for the production of a pharmaceutical composition for the treatment of a disease caused by a retrovirus infection, which comprises incorporating in said pharmaceutical composition, a compound of the formula 1'

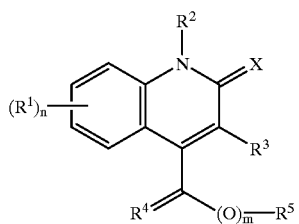

(I')

or a tautomeric form thereof, of the formula I'a

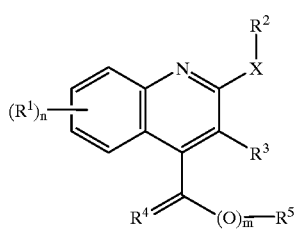

(I'a)

in which
  n is zero, one, two, three or four,
  the individual substituents $R^1$ independently of one another are fluorine, chlorine, bromine, iodine, trifluoromethyl, trifluoromethoxy, hydroxyl, alkyl, cycloalkyl, alkoxy, alkoxy(alkoxy), alkylthio, alkylsulfinyl, alkylsulfonyl, nitro, amino, azido, alkylamino, dialkylamino, piperidino, morpholino, 1-pyrrolidinyl, acyl, acyloxy, acylamino, cyano, carbamoyl, carboxyl, alkyloxycarbonyl, hydroxysulfonyl, sulfamoyl, or
    a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, heteroaroyl, heteroaryl or heteroarylmethyl radical, each of which is unsubstituted or substituted by up to five radicals $R^6$ which are independent of one another,
  where $R^6$ is
    fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, alkyloxycarbonyl, phenyl, phenoxy or heteroaryl,
  X is oxygen, sulfur, selenium or substituted nitrogen N—$R^2$, N—O—$R^2$, in which $R^2$ has one of the meanings given below,
  and $R^2$ is hydrogen,
    alkyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
    alkenyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
    alkynyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
    cycloalkyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
    cycloalkenyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
    (cycloalkyl)-(alkyl), which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
    (cycloalkenyl)-(alkyl), which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
    alkylcarbonyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;
    alkenylcarbonyl, which is unsubstituted or substituted by fluorine, chlorine or hydroxyl, alkoxy, oxo, phenyl;
    (cycloalkyl)carbonyl, which is unsubstituted or substituted by fluorine, chlorine or hydroxyl, alkoxy, oxo, phenyl;
    (cycloalkenyl)carbonyl, which is unsubstituted or substituted by fluorine, chlorine or hydroxyl, alkoxy, oxo, phenyl;
    (cycloalkyl)-(alkyl)carbonyl, which is unsubstituted or substituted by fluorine, chlorine or hydroxyl, alkoxy, oxo, phenyl;
    (cycloalkenyl)-(alkyl)carbonyl, which is unsubstituted or substituted by fluorine, chlorine or hydroxyl, alkoxy, oxo, phenyl;
    alkyloxycarbonyl, which is unsubstituted or substituted by fluorine, chlorine, bromine, hydroxyl, alkoxy, alkylamino, dialkylamino, alkylthio;
    alkenyloxycarbonyl, which is unsubstituted or substituted by fluorine, chlorine, hydroxyl, alkoxy, oxo, phenyl;
    alkynyloxycarbonyl, which is unsubstituted or substituted by fluorine, chlorine, hydroxyl, alkoxy, oxo, phenyl;
    alkylthiocarbonyl, which is unsubstituted or substituted by fluorine, chlorine, hydroxyl, alkoxy, oxo, phenyl;
    alkenylthiocarbonyl, which is unsubstituted or substituted by fluorine, chlorine, hydroxyl, alkoxy, oxo, phenyl;
    alkylamino and dialkylaminocarbonyl, each of which is unsubstituted or substituted by fluorine, chlorine, hydroxyl, alkoxy, oxo, phenyl;

alkenylamino and dialkenylaminocarbonyl, each of which is unsubstituted or substituted by fluorine, chlorine, hydroxyl, alkoxy, oxo, phenyl;

alkylsulfonyl, which is unsubstituted or substituted by fluorine, chlorine, hydroxyl, alkoxy, alkylthio, oxo, phenyl;

alkenylsulfonyl, which is unsubstituted or substituted by fluorine, chlorine, hydroxyl, alkoxy, oxo, phenyl;

aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl, arylalkoxycarbonyl, each of which is substituted by up to five radicals $R^6$ which are independent of one another, where $R^6$ is as defined above;

or heteroaryl, heteroarylalkyl, heteroarylalkenyl, heteroarylalkylcarbonyl or heteroarylalkenylcarbonyl, each of which is substituted by up to three radicals $R^6$ which are independent of one another, where $R^6$ is as defined above, and $R^3$ is hydrogen, cyano, alkyl, which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

alkyloxy, which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

alkenyl, which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkyl, which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkenyl, which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

or aryl, arylalkyl, heteroaryl or heteroarylalkyl, each of which is substituted by up to five radicals $R^6$ which are independent of one another, where $R^6$ is as defined above, and $R^4$ is oxygen, sulfur, $NOR^2$, NOH, where $R^2$ is as defined above, or $R^4$ is an aryl radical bonded via a double bond, which is unsubstituted or substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl, or $R^4$ is two hydrogen atoms residing on the linking carbon atom, where in this case additionally to the definitions indicated below for $R^5$ this radical can also be alkylcarbonyl, and in which m is 0 or 1, and $R^5$ is hydrogen, alkyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkenyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkynyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkenyl, which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

(cycloalkyl)-(alkyl), which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

(cycloalkenyl)-(alkyl), which is unsubstituted or substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxof carboxyl, carbamoyl;

or aryl, arylalkyl, arylalkenyl, arylalkynyl, each of which is substituted by up to five radicals $R^6$ which are independent of one another, where $R^6$ is as defined above;

or heteroaryl, heteroarylalkyl, heteroarylalkenyl, each of which is substituted by up to three radicals $R^6$ which are independent of one another, where $R^6$ is as defined above, or an optical isomer, a diastereomer in pure form, or a mixture of diastereomers in pure form, an addition salt, or a prodrug thereof.

7. A process for the preparation of a compound as claimed in claim 1, which comprises a) for the preparation of a compound of the formula I or Ia in which X and $R^4$ are oxygen, m is 1, with the other radicals are as defined in claim 1, reacting a compound of the formula II where A is a leaving group, with a compound of the formula III where m is hydrogen, a metal atom or a metal atom equivalent,

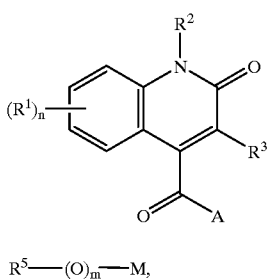

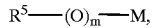

or b) reacting a compound of the formula I where X is oxygen, and $R^1$ to $R^5$ are as defined in claim 1, with a sulfurizing reagent to give a compound of the formula I where X is sulfur and $R^1$ to $R^5$ are as defined in claim 1, or c) reacting a compound of the formula I where $R^1$–$R^5$ are as defined in claim 1 and X is an oxygen or sulfur atom, with a compound of the formula IV or IVa

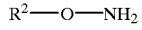

to give a derivative of the formula I where $R^1$–$R^5$ are as defined in claim 1 and X is N—$R^2$ or N—O—$R^2$ or d) reacting a compound of the formula II where A is chlorine and $R^1$ to $R^5$ are as defined in claim 1 with a reductant to give a compound of the formula I where $R^1$ to $R^3$ are as defined above, $R^4$ together with the linking carbon atom forming a $CH_2$ group and $(O)_m$—$R^5$ being hydroxyl,

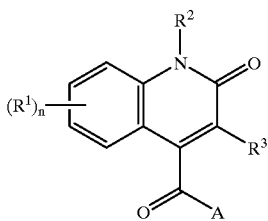

or e) reacting a compound of the formula I or Ia where $R^2$ is hydrogen and $R^1$, $R^3$, $R^4$ and $R^5$ are as defined in claim 1, with a compound of the formula V

R(2)—B  (V), where B is a leaving group, to give derivatives of the formula I in which the definitions described in claim 1 for a compound of the formula I or Ia apply to $R^2$ with the exception of $R^2$ is hydrogen.

8. A pharmaceutical composition comprising an effective amount of at least one compound of the formula I or Ia as claimed in claim 1 together with a pharmaceutically acceptable carrier.

9. A process for the production of a pharmaceutical composition as claimed in claim 8, which comprises brining a compound of the formula I or Ia into a suitable administration form with a pharmaceutically acceptable carrier.

10. A process as claimed in claim 7, wherein A is a halogen atom, and the metal is an alkali metal or an alkaline earth metal.

11. A method for the treatment of a disease caused by a retrovirus which comprises administering to a host in need of said treatment a pharmaceutical composition comprising an effective amount of at least one compound of formula I or Ia as claimed in claim 1 and a pharmaceutically acceptable carrier.

12. A method for the treatment of a disease caused by a retrovirus which comprises administering to a host in need of said treatment an effective amount of a compound of the formula I or Ia as claimed in claim 1.

13. The compound of claim 1, wherein said compound is chosen from prodrugs of said formulae I and Ia.

14. The compound of claim 2, wherein said compound is chosen from prodrugs of said formulae I and Ia.

15. The compound of claim 3, wherein said compound is chosen from prodrugs of said formulae I and Ia.

16. The compound of claim 4, wherein said compound is chosen from prodrugs of said formulae I and Ia.

17. The compound of claim 5, wherein said compound is chosen from prodrugs of said formulae I and Ia.

18. The process of claim 6, wherein said compound is chosen from prodrugs of said formulae I' and I'a.

19. The method of claim 11 wherein said compound is chosen from prodrugs of said formulae I and Ia.

* * * * *

UNITED STATES PATENT AND TRADEMARK OFFICE
CERTIFICATE OF CORRECTION

PATENT NO.: 6,114,349

DATED: September 5, 2000

INVENTORS: Reinhard KIRSCH et al.

It is certified that an error appears in the above-identified patent and that said Letters Patent is hereby corrected as shown below:

In Claim 1, col. 72, line 15, "(cycloalkenyl," should read --cycloalkenyl,--.
In Claim 1, col. 73, line 15, "aralkynyl" should read --arylalkynyl--.
In Claim 1, col. 73, line 53, "substitute" should read --substituted--.
In Claim 2, col. 75, line 65, after "meanings", delete the comma.
In Claim 3, col. 80, line 38, "on another" should read --one another--.
In Claim 3, col. 80, line 45, after "in pure form", insert a comma.
In Claim 4, col. 80, line 48, after "one", insert a comma.
In Claim 4, col. 81, line 66, "on another" should read --one another--.
In Claim 6, col. 86, line 46, "thioxof" should read --thioxo,--.
In Claim 6, col. 86, line 57, "an addition" should read --or addition--.
In Claim 6, col. 86, line 58, after "salt", delete ", or a prodrug".
In Claim 9, col. 88, line 19, "brining" should read --bringing--.

Signed and Sealed this

Seventeenth Day of April, 2001

Attest:

NICHOLAS P. GODICI

Attesting Officer     Acting Director of the United States Patent and Trademark Office